(12) United States Patent
Jørgensen et al.

(10) Patent No.: US 6,555,348 B2
(45) Date of Patent: Apr. 29, 2003

(54) ENZYME ISOLATED FROM A BIFIDOBACTERIUM

(75) Inventors: Flemming Jørgensen, Lyngby (DK); Ole Cai Hansen, Værløse (DK); Peter Stougaard, Skibby (DK)

(73) Assignee: Arla Foods AMBA (DK)

( * ) Notice: Subject to any disclaimer, the term of this patent is extended or adjusted under 35 U.S.C. 154(b) by 0 days.

(21) Appl. No.: 09/865,621

(22) Filed: May 29, 2001

(65) Prior Publication Data

US 2002/0086358 A1 Jul. 4, 2002

Related U.S. Application Data

(60) Provisional application No. 60/207,154, filed on May 26, 2000.

(51) Int. Cl.$^7$ ............................ C12P 19/44; C12N 9/10; C12N 9/26; A23C 19/00; A23C 17/00
(52) U.S. Cl. ........................ 435/74; 435/193; 435/201; 426/582; 426/583
(58) Field of Search ................................. 435/201, 193, 435/74; 426/582, 583

(56) References Cited

U.S. PATENT DOCUMENTS 5,939,289 A  *  8/1999  Ertesvag et al. .............. 435/72

OTHER PUBLICATIONS

V. Dumortier, et al. "Purification and Properties of a β–D–Galactosidase From *Bifidobacterium bifidum* Exhibiting A Transgalactosylation Reaction", Biotechnology. Appl. Biochem., vol. 19, pp. 341–354 (1994).

N. Onishi et al., "Purification and Properties of a Novel Thermostable Galacto–Oligosaccharide–Producing β–Galactosidase From *Sterigmatomyces elviae* CBS8119", Applied and Envornmental Microbiology, vol. 61, No. 11, pp. 4026–4030, (Nov. 1995).

M. Nakao et al., "Purification and Characterization of a Thermostable β–Galactosidase with High Transgalactosylation Activity From *Saccharopolyspora rectivirgula*", Appl. Microbiol Biotechnol., vol. 40, pp. 657–663; (1994).

R.E. Huber, et al., "A Quantitation of the Factors which Affect the Hydrolase and Transgalactosylase Activities of β–Galactosidase (*E. coli*) on Lactose", Biochemistry, vol. 15, No. 9, pp. 1994–2001, (1976).

M.V.W. Wijnands, et al., "A Comparison of the Effects of Dietary Cellulose and Fermentable Galacto–Oligsaccharide, in a Rat Model of Colorectal Carcinogenesis: Fermentable Fibre Confers Greater Protection Then Non–Fermentable Fibre in Both High and Low Fat Backgrounds", Carcinogenesis, vol. 20, No. 4, pp. 651–656; (1999).

* cited by examiner

*Primary Examiner*—Elizabeth Slobodyansky
(74) *Attorney, Agent, or Firm*—Finnegan, Henderson, Farabow, Garrett & Dunner, LLP

(57) ABSTRACT

The present invention concerns a new β-galactosidase with transgalactosylating activity isolated from *Bifidobacterium bifidum* and a truncated enzyme where the C-terminal end of the β-galactosidase protein has been deleted, resulting in an enzyme with a higher transgalactosylating activity than hydrolase activity. When lactose is used as a substrate, galacto-oligosaccharides are products of the transgalactosylase activity. Galacto-oligosaccharides enhance growth of health-promoting Bifidobacterium that may be used in a number of applications in the dairy industry.

12 Claims, 10 Drawing Sheets

```
   1 ATGCGTTGCGTTGCGATTTTTCCGGCCCTGTATGGGGATACAGGATTGGCGATGGCGACACGCCGTTTTGTTAATGGC
  81 ATTTACATGAAATACAGGTAATGAGATATCATTCTCATGATCACCGTGTGGATATCGCATTGGTGCGTATACACTAACAG
 161 CAACAGAGCGGCGCGGCAGGCGCTCGTGGATTCAATGAAGAAGGAACGTTTATGGCAGTTCGCAGACTTGGTGGCCGCAT
                                                          M  A  V  R  R  L  G  G  R  I
 241 CGTGGCTTTCGCCGCCACAGTGGCCTTGTCAATACCGTTAGGGTTGTTAACAAATTCAGCGTGGGCGGTCGAGGACGCCA
     V  A  F  A  A  T  V  A  L  S  I  P  L  G  L  L  T  N  S  A  W  A  V  E  D  A
 321 CCCGATCCGACTCCACCACGCAGATGAGCTCCACGCCGGAGGTGGTCTACTCAGCGCCGTGGATTCCAAGCAGAATCGC
     T  R  S  D  S  T  T  Q  M  S  S  T  P  E  V  V  Y  S  S  A  V  D  S  K  Q  N  R
 401 ACCTCGGATTTCGACGCCAACTGGAAGTTCATGCTGTCCGATTCCGTGCAGGCGCAGGATCCGGCGTTCGACGATTCGGC
     T  S  D  F  D  A  N  W  K  F  M  L  S  D  S  V  Q  A  Q  D  P  A  F  D  D  S  A
 481 CTGGCAGCAGGTCGACCTGCCGCATGACTACAGCATCACGCAGAAGTATTCGCAGAGCAACGAGGCCGAAAGCGCATACC
     W  Q  Q  V  D  L  P  H  D  Y  S  I  T  Q  K  Y  S  Q  S  N  E  A  E  S  A  Y
 561 TTCCCGGCGGCACCGGCTGGTACCGCAAGTCCTTCACCATCGACCGGGACCTCGCCGGCAAGCGCATCGCCATCAACTTC
     L  P  G  G  T  G  W  Y  R  K  S  F  T  I  D  R  D  L  A  G  K  R  I  A  I  N  F
 641 GACGGCGTGTACATGAACGCCACCGTCTGGTTCAACGGCGTCAAGCTCGGCACCCATCCGTACGGCTACTCGCCGTTCTC
     D  G  V  Y  M  N  A  T  V  W  F  N  G  V  K  L  G  T  H  P  Y  G  Y  S  P  F  S
 721 CTTCGACCTGACCGGCAACGCCAAGTTCGGTGGGGAGAACACCATCGTCGTCAAGGTCGAGAACAGGCTGCCGTCCAGCC
     F  D  L  T  G  N  A  K  F  G  G  E  N  T  I  V  V  K  V  E  N  R  L  P  S  S
 801 GCTGGTACTCCGGCTCCGGCATCTACCGCGACGTCACCCTCACCGTCACCGACGGCGTGCACGTCGGCAATAACGGCGTG
     R  W  Y  S  G  S  G  I  Y  R  D  V  T  L  T  V  T  D  G  V  H  V  G  N  N  G  V
 881 GCCATCAAGACCCCGAGCCTCGCCACCCAAAACGGCGGCGACGTGACGATGAACCTCACCACCAAGGTCGCCAACGACAC
     A  I  K  T  P  S  L  A  T  Q  N  G  G  D  V  T  M  N  L  T  T  K  V  A  N  D  T
 961 CGAGGCCGCGGCGAACATCACCCTCAAGCAGACCGTGTTCCCCAAGGGAGGCAAGACCGACGCCGCCATCGGCACCGTCA
     E  A  A  A  N  I  T  L  K  Q  T  V  F  P  K  G  G  K  T  D  A  A  I  G  T  V
1041 CCACCGCATCCAAGTCCATCGCGGCCGGTGCCAGCGCGGACGTGACCTCCACGATCACCGCCGCTTCGCCCAAGCTGTGG
     T  T  A  S  K  S  I  A  A  G  A  S  A  D  V  T  S  T  I  T  A  A  S  P  K  L  W
1121 AGCATCAAGAACCCGAACCTGTACACCGTGCGCACCGAAGTGCTCAACGGCGGCAAGGTGCTCGACACTTACGACACCGA
     S  I  K  N  P  N  L  Y  T  V  R  T  E  V  L  N  G  G  K  V  L  D  T  Y  D  T  E
1201 ATATGGCTTCCGCTGGACCGGCTTCGATGCGACCAGCGGTTTCTCGCTCAACGGCGAGAAAGTCAAGCTCAAGGGCGTCT
     Y  G  F  R  W  T  G  F  D  A  T  S  G  F  S  L  N  G  E  K  V  K  L  K  G  V
1281 CAATGCATCATGACCAGGGATCGCTCGGCGCGGTCGCCAACCGCCGCGCCATCGAGCGCCAGGTCGAGATTCTCCAGAAG
     S  M  H  H  D  Q  G  S  L  G  A  V  A  N  R  R  A  I  E  R  Q  V  E  I  L  Q  K
1361 ATGGGCGTCAACTCGATCCGCACCACGCACAACCCCGCAGCCAAGGCGCTGATTGACGTCTGCAACGAGAAGGGCGTCCT
     M  G  V  N  S  I  R  T  T  H  N  P  A  A  K  A  L  I  D  V  C  N  E  K  G  V  L
1441 CGTGGTCGAAGAGGTCTTCGACATGTGGAACCGGTCGAAGAACGGCAACACCGAGGATTACGGCAAGTGGTTCGGCCAGG
     V  V  E  E  V  F  D  M  W  N  R  S  K  N  G  N  T  E  D  Y  G  K  W  F  G  Q
1521 CCATCGCCGGTGACAACGCCGTCCTGGGTGGCGACAAGGACGAGACCTGGGCCAAGTTCGACCTGACCAGCACCATCAAC
     A  I  A  G  D  N  A  V  L  G  G  D  K  D  E  T  W  A  K  F  D  L  T  S  T  I  N
1601 CGTGACAGGAACGCCCCGTCCGTCATCATGTGGTCGCTCGGCAACGAGATGATGGAAGGCATCAGCGGCAGCGTCTCGGG
     R  D  R  N  A  P  S  V  I  M  W  S  L  G  N  E  M  M  E  G  I  S  G  S  V  S  G
1681 CTTCCCGGCTACCTCCGCCAAGCTGGTCGCATGGACGAAGGCCGCGGACAGCACCCGCCCGATGACCTACGGCGACAACA
     F  P  A  T  S  A  K  L  V  A  W  T  K  A  A  D  S  T  R  P  M  T  Y  G  D  N
1761 AGATCAAGGCCAACTGGAACGAGTCGAACACCATGGGCGACAACCTGACCGCCAACGGCGGCGTGGTCGGCACCAACTAC
     K  I  K  A  N  W  N  E  S  N  T  M  G  D  N  L  T  A  N  G  G  V  V  G  T  N  Y
1841 TCCGACGGCGCGAACTACGACAAGATCCGCACGACCCACCCCTCATGGGCCATCTATGGTTCCGAGACGGCGTCCGCCAT
     S  D  G  A  N  Y  D  K  I  R  T  T  H  P  S  W  A  I  Y  G  S  E  T  A  S  A  I
1921 CAACAGCCGAGGCATCTACAACCGCACCACCGGCGGCGCCCAGTCAAGCGACAAGCAGCTGACCAGCTATGACAATTCCG
     N  S  R  G  I  Y  N  R  T  T  G  G  A  Q  S  S  D  K  Q  L  T  S  Y  D  N  S
2001 CAGTCGGCTGGGGCGCCGTCGCCAGCTCCGCCTGGTACGACGTGGTCCAGCGCGATTTCGTCGCCGGCACATACGTGTGG
     A  V  G  W  G  A  V  A  S  S  A  W  Y  D  V  V  Q  R  D  F  V  A  G  T  Y  V  W
2081 ACCGGCTTCGACTACCTCGGCGAACCCACCCCGTGGAACGGCACCGGCTCCGGCGCCGTGGGCTCCTTGGCCGTCGCCGA
     T  G  F  D  Y  L  G  E  P  T  P  W  N  G  T  G  S  G  A  V  G  S  L  A  V  A  E
2161 AGAACTCGTACTTCGGCATCGTCGACACCGCAGGCTTCCCGAAGACACCTATTACTTCTATCAGAGCCAGTGGAACGACG
     E  L  V  L  R  H  R  R  H  R  R  L  P  E  D  T  Y  Y  F  Y  Q  S  Q  W  N  D
2241 ACGTGCACACGCTGCACATCCTCCCCGCATGGAACGAGAACGTCGTCGCCAAGGGCTCCGGCAACAACGTGCCGGTCGTC
     D  V  H  T  L  H  I  L  P  A  W  N  E  N  V  V  A  K  G  S  G  N  N  V  P  V  V
```

FIG. 1(A)

```
2321  GTCTACACCGACGCGGCCAAGGTCAAGCTGTACTTCACACCGAAGGGCAGTACCGAAAAGCGACTGATCGGAGAGAAGTC
       V  Y  T  D  A  A  K  V  K  L  Y  F  T  P  K  G  S  T  E  K  R  L  I  G  E  K  S

2401  CTTCACCAAGAAGACCACCGCGGCCGGATACACCTATCAGGTCTACGAGGGCTCCGACAAGGACTCCACCGCCCACAAGA
       F  T  K  K  T  T  A  A  G  Y  T  Y  Q  V  Y  E  G  S  D  K  D  S  T  A  H  K

2481  ACATGTACCTGACCTGGAACGTGCCGTGGGCCGAGGGCACCATCTCCGCCGAAGCATACGACGAGAACAACAGGCTGATC
       N  M  Y  L  T  W  N  V  P  W  A  E  G  T  I  S  A  E  A  Y  D  E  N  N  R  L  I

2561  CCCGAGGGGTCCACCGAGGGCAACGCGTCGGTGACCACCACCGGCAAGGCCGCGAAGCTTAAAGCCGATGCCGACCGCAA
       P  E  G  S  T  E  G  N  A  S  V  T  T  T  G  K  A  A  K  L  K  A  D  A  D  R  K

2641  GACGATCACCGCGGACGGCAAGGACCTGTCGTACATCGAGGTCGACGTGACCGACGCCAACGGCCATATCGTCCCCGATG
       T  I  T  A  D  G  K  D  L  S  Y  I  E  V  D  V  T  D  A  N  G  H  I  V  P  D

2721  CCGCCAACCGCGTCACCTTCGACGTCAAGGGCGCCGGCAAACTGGTCGGCGTCGACAACGGCAGCTCGCCGGATCACGAC
       A  A  N  R  V  T  F  D  V  K  G  A  G  K  L  V  G  V  D  N  G  S  S  P  D  H  D

2801  TCCTATCAGGCCGACAACCGCAAGGCGTTCAGCGGCAAGGTGCTCGCCATCGTCCAGTCCACCAAGGAGGCGGGCGAGAT
       S  Y  Q  A  D  N  R  K  A  F  S  G  K  V  L  A  I  V  Q  S  T  K  E  A  G  E  I

2881  CACCGTCACCGCCAAGGCCGACGGTCTGCAATCATCCACAGTGAAGATCGCCACCACCGCCGTCCCCGGCACCAGCACCG
       T  V  T  A  K  A  D  G  L  Q  S  S  T  V  K  I  A  T  T  A  V  P  G  T  S  T

2961  AGAAGACGGTCCGCAGCTTCTACTACTCGCGCAACTACTACGTCAAGACCGGCAACAAGCCGATTCTGCCGAGTGATGTC
       E  K  T  V  R  S  F  Y  Y  S  R  N  Y  Y  V  K  T  G  N  K  P  I  L  P  S  D  V

3041  GAGGTGCGCTACTCCGACGGCACGTCGGACCGTCAGAACGTCACATGGGACGCAGTCAGCGACGACCAGATCGCCAAGGC
       E  V  R  Y  S  D  G  T  S  D  R  Q  N  V  T  W  D  A  V  S  D  D  Q  I  A  K  A

3121  CGGTTCGTTCAGCGTGGCCGGCACGGTCGCCGGGCAGAAGATCTCCGTGCGCGTGACGATGATCGACGAGATCGGTGCGC
       G  S  F  S  V  A  G  T  V  A  G  Q  K  I  S  V  R  V  T  M  I  D  E  I  G  A

3201  TGCTCAACTATTCGGCCAGCACACCGGTCGGCACGCCCGCCGTGCTGCCTGGCTCGCGTCCGGCCGTGCTGCCCGACGGC
       L  L  N  Y  S  A  S  T  P  V  G  T  P  A  V  L  P  G  S  R  P  A  V  L  P  D  G

3281  ACCGTGACCAGCGCGAACTTCGCCGTCCACTGGACCAAGCCCGCCGACACCGTGTACAACACGGCCGGCACCGTCAAGGT
       T  V  T  S  A  N  F  A  V  H  W  T  K  P  A  D  T  V  Y  N  T  A  G  T  V  K  V

3361  CCCCGGCACCGCCACCGTCTTCGGCAAGGAGTTCAAGGTCACCGCGACGATTCGCGTGCAGCGGTCGCAGGTCACCATCG
       P  G  T  A  T  V  F  G  K  E  F  K  V  T  A  T  I  R  V  Q  R  S  Q  V  T  I

3441  GCAGCAGCGTCTCCGGCAATGCGCTGCGCCTGACTCAGAACATCCCCGCCGACAAGCAGTCCGACACGCTGGACGCCATC
       G  S  S  V  S  G  N  A  L  R  L  T  Q  N  I  P  A  D  K  Q  S  D  T  L  D  A  I

3521  AAGGACGGCTCCACGACCGTCGACGCCAATACCGGCGGCGGCGCGAACCCGTCAGCATGGACCAACTGGGCGTACTCGAA
       K  D  G  S  T  T  V  D  A  N  T  G  G  G  A  N  P  S  A  W  T  N  W  A  Y  S  K

3601  GGCCGGCCACAACACCGCCGAGATCACCTTCGAGTACGCGACCGAGCAGCAGCTCGGCCAGATTGTCATGTACTTCTTCC
       A  G  H  N  T  A  E  I  T  F  E  Y  A  T  E  Q  Q  L  G  Q  I  V  M  Y  F  F

3681  GCGACAGCAACGCGGTGAGGTTCCCCGACGCCGGCAAGACGAAGATCCAGATCTCCGCGGACGGCAAGAACTGGACGGAT
       R  D  S  N  A  V  R  F  P  D  A  G  K  T  K  I  Q  I  S  A  D  G  K  N  W  T  D

3761  CTCGCTGCCACGGAGACCATCGCGGCCCAGGAGTCGTCCGACCGAGTCAAGCCGTACACCTATGACTTCGCTCCGGTGGG
       L  A  A  T  E  T  I  A  A  Q  E  S  S  D  R  V  K  P  Y  T  Y  D  F  A  P  V  G

3841  AGCCACGTTCGTCAAGGTCACGGTCACCAACGCCGACACCACAACCCCCAGCGGCGTGGTCTGCGCCGGCCTGACCGAGA
       A  T  F  V  K  V  T  V  T  N  A  D  T  T  T  P  S  G  V  V  C  A  G  L  T  E

3921  TCGAGCTGAAGACCGCGACCAGCAAGTTCGTCACGAACACGTCCGCCGCGCTCTCGTCGCTGACAGTGAACGGCACGAAG
       I  E  L  K  T  A  T  S  K  F  V  T  N  T  S  A  A  L  S  S  L  T  V  N  G  T  K

4001  GTCTCCGACTCCGTGCTCGCCGCCGGCTCCTACAACACGCCCGCGATCATCGCGGACGTCAAAGCCGAGGGCGAAGGCAA
       V  S  D  S  V  L  A  A  G  S  Y  N  T  P  A  I  I  A  D  V  K  A  E  G  E  G  N

4081  CGCCAGCGTCACCGTGCTGCCCGCGCACGACAACGTGATCCGCGTGATCACCGAGTCCGAGGACCACGTCACGCGCAAGA
       A  S  V  T  V  L  P  A  H  D  N  V  I  R  V  I  T  E  S  E  D  H  V  T  R  K

4161  CCTTCACCATCAACCTGGGCACGGAGCAGGAATTCCCCGCAGACTCCGATGAACGCGACTACCCGGCCGCCGACATGACG
       T  F  T  I  N  L  G  T  E  Q  E  F  P  A  D  S  D  E  R  D  Y  P  A  A  D  M  T

4241  GTCACCGTGGGCAGCGAACAGACGTCCGGCACCGCGACCGAAGGCCCGAAGAAATTCGCGGTCGACGGCAACACCAGCAC
       V  T  V  G  S  E  Q  T  S  G  T  A  T  E  G  P  K  K  F  A  V  D  G  N  T  S  T

4321  GTACTGGCATTCCAACTGGACGCCCACCACCGTGAACGACCTGTGGATCGCCTTCGAGCTCCAGAAACCCACCAAGCTCG
       Y  W  H  S  N  W  T  P  T  T  V  N  D  L  W  I  A  F  E  L  Q  K  P  T  K  L

4401  ACGCGCTGCGCTACCTGCCGCGCCCCGCGGGCAGCAAGAACGGCTCCGTCACCGAATACAAGGTTCAGGTCAGCGATGAC
       D  A  L  R  Y  L  P  R  P  A  G  S  K  N  G  S  V  T  E  Y  K  V  Q  V  S  D  D

4481  GGCACCAACTGGACCGACGCGGGCTCCGGCACATGGACCACCGATTACGGCTGGAAGCTCGCCGAGTTCAATCAGCCGGT
       G  T  N  W  T  D  A  G  S  G  T  W  T  T  D  Y  G  W  K  L  A  E  F  N  Q  P  V
```

FIG. 1(B)

```
4561  GACCACCAAGCACGTGCGGCTCAAGGCCGTCCACACCTATGCGGATTCCGGCAACGACAAGTTCATGTCCGCCTCCGAAA
       T  T  K  H  V  R  L  K  A  V  H  T  Y  A  D  S  G  N  D  K  F  M  S  A  S  E

4641  TCCGCCTGCGCAAGGCCGTCGACACCACCGACATCAGCGGCGCGACCGTGACCGTGCCCGCCAAGCTGACCGTCGACCGG
       I  R  L  R  K  A  V  D  T  T  D  I  S  G  A  T  V  T  V  P  A  K  L  T  V  D  R

4721  GTGGACGCCGACCATCCCGCCACCTTCGCCACGAAGGACGTGACGGTGACGTTGGGCGACGCCACGCTGCGCTACGGCGT
       V  D  A  D  H  P  A  T  F  A  T  K  D  V  T  V  T  L  G  D  A  T  L  R  Y  G  V

4801  GGACTACCTGCTCGACTACGCGGGCAACACCGCCGTCGGCAAGGCCACGGTGACCGTGCGCGGCATCGACAAGTACTCCG
       D  Y  L  L  D  Y  A  G  N  T  A  V  G  K  A  T  V  T  V  R  G  I  D  K  Y  S

4881  GCACCGTCGCCAAGACGTTCACCATCGAACTGAAGAACGCCCCGGCGCCGGAACCGACGCTGACCTCGGTGAGCGTCAAG
       G  T  V  A  K  T  F  T  I  E  L  K  N  A  P  A  P  E  P  T  L  T  S  V  S  V  K

4961  ACCAAGCCTTCCAAGCTGACCTATGTGGTCGGCGACGCGTTCGACCCGGCAGGACTGGTGCTGCAGCACGACAGACAGGC
       T  K  P  S  K  L  T  Y  V  V  G  D  A  F  D  P  A  G  L  V  L  Q  H  D  R  Q  A

5041  CGATCGCCCCCCACAGCCACTTGTTGGAGAACAGGCCGACGAACGCGGACTGACGTGCGGAACGCGATGCGATCGCGTTG
       D  R  P  P  Q  P  L  V  G  E  Q  A  D  E  R  G  L  T  C  G  T  R  C  D  R  V

5121  AACAGCTGCGCAAACACGAGAATCGTGAAGCCCATCGTACGGGCCTCGATCATCTGGAATTCGTGGGTGCCGCCGATGGA
       E  Q  L  R  K  H  E  N  R  E  A  H  R  T  G  L  D  H  L  E  F  V  G  A  A  D  G

5201  GCGGTCGGTGAACAGGCCACCTTCAAGGTGCATGTCCATGCCGATCAAGGTGACGGCCGCCATGATGATGCCGATGAACG
       A  V  G  E  Q  A  T  F  K  V  H  V  H  A  D  Q  G  D  G  R  H  D  D  A  D  E  R

5281  CGATATCGATCCACATGTCCCTGTCGATCACGCGGTCGGTGAGCTTGCGCGGGCTGCGTGCCATCACGTCATCGGTCTGC
       D  I  D  P  H  V  P  V  D  H  A  V  G  E  L  A  R  A  A  C  H  H  V  I  G  L

5361  GGGTCGACACCCATCGCCTCAAGGCATCCGGCTTCCAGATCCCCGCCGACGACATGGCCGAGATCGACCGCATCACCGGC
       R  V  D  T  H  R  L  K  A  S  G  F  Q  I  P  A  D  D  M  A  E  I  D  R  I  T  G

5441  TTCCACCGCTTCGAGCGCCACGTCGGCTGACGTGATTGGGCTTCCCCGCTGTCTGGTGCCGGCTCGCGA (SEQ ID NO:1)
       F  H  R  F  E  R  H  V  G  Z
                                                                          (SEQ ID NO:2)
```

FIG. 1(C)

| | |
|---|---|
| L35444 | RFLAASQAY--LDALAKQVQPLLN-HNGGP-II-AVQVE-NEYGSYAD (SEQ ID NO:9) |
| M13466 | HYCPNHPQL--ITHIKRLVRAIAERYKNHPALK-MWHVN-NEYACHVS (SEQ ID NO:10) |
| U17417 | TISSSAWYYSVGQYAAKMTRALAERYKDHPALA-LWHVD-NELGCHVS (SEQ ID NO:11) |
| E05040 | HWRATSPVF--LDYALNLCRKMAEHYKDNPYVV-SWHVS-NEYGCHNR (SEQ ID NO:12) |
| OLGA88 | HWRPTSPVF--REYALRLCRAMAEHYRDNPYVV-AWHVS-NEYGCHNR (SEQ ID NO:13) |
| L03424 | NSCPNSPTY--RKYSEKIADKLAERYKDHPAVL-VWHIS-NEYGGDCY (SEQ ID NO:14) |
| L03425 | NHCYTSPVY--REKVTAINTKLAERYSDHPAVI-GWHIS-NEFGGDCH (SEQ ID NO:15) |
| D49537 | NHCYTSPIY--REKIAIIDRLLAERYKDHPALI-LWHIS-NEFEGQCY (SEQ ID NO:16) |
| L20757 | RWGGME-TG--GNPERPPHRSSATG--TTRLSY-IWGVRINESQDSHD (SEQ ID NO:17) |
| M57579 | QYIGNS-EW--KKVAEQNLREMITRDWNHPSII-LWGVRINESQDDDA (SEQ ID NO:18) |
| Y08557 | QHIGDE-NW--KNIAKENLKEMILRDRNHPCIF-MWGVRINERLDDHD (SEQ ID NO:19) |
| OLGA5 | AVLGGDKDE--TWAKFD-LTSTINRDRNAPSVI-MWSLG-NEMMEGIS (SEQ ID NO:20) |
| M63636 | NIPASEPEW--LPACLDRANNMFQRDKNHASVI-IWSCG-NESYAGKD (SEQ ID NO:21) |
| M35107 | NVPGSLPQW--QAAVLDRASSMVERDKNHPSVL-IWSCG-NESYAGED (SEQ ID NO:22) |
| M92281 | NVPGDNPHW--PAAVIDRARSNYEWFKNHPSII-FWSLG-NESYAGED (SEQ ID NO:23) |
| X82287 | NVPGSYDEW--EAATLDRARTNFETFKNHVSIL-FWSLG-NESYAGSV (SEQ ID NO:24) |
| M23530 | NVPGDDQHW--LGASLSRVKNMMARDKNHASIL-IWSLG-NESYAGTV (SEQ ID NO:25) |
| AJ242596 | IVPGSKREW--EGACVDRVNSMMRRDYNHPSVL-IWSLG-NESYVGDV (SEQ ID NO:26) |
| OLGA2 | SVPGDDEAW--LGACIDRLDSMILRDNHPSVL-VWSLG-NESYAGEV (SEQ ID NO:27) |
| U62625 | CYFARDPLF--KKAILDRQQANVERDKNRTSII-IWSLG-NEAGYGAN (SEQ ID NO:28) |
| Y14599 | NIIADDSKF--ETAIIERIEASIMPLKNYSSIV-SWSLG-NESGFGKN (SEQ ID NO:29) |
| U08186 | VTLANRWEW--EKAHFDRIKRMVERDKNHPSII-FWSLG-NEAGDGVN (SEQ ID NO:30) |
| OLGA1 | RPIADNPAW--IAPTVDRAQRSVERDKNHASII-FWSMG-NECAYGCT (SEQ ID NO:31) |
| M11441 | NRLSDDPAW--LPAFSARVTRMVQSNRNHPCII-IWSLG-NESGGGGN (SEQ ID NO:32) |
| U60828 | NRLTNDPTY--LPLMSERVTRMVMRDRNHPSII-IWSLG-NESGYGSN (SEQ ID NO:33) |
| J01636 | NRLTDDPRW--LPAMSERVTRMVQRDRNHPSVI-IWSLG-NESGHGAN (SEQ ID NO:34) |
| D42077 | SRLADDPRW--LPAMSERVTRMVQRDRNHPSII-IWSLG-NESGHGAN (SEQ ID NO:35) |
| D37882 (P) | EGLHEDGDFLTHEKMDDFVEYADYCFKEFPEVK-YWITI-NEIRSVAV (SEQ ID NO:36) |
| J03479 (P) | EVLHKDGDFLNRKTIDYFVDYAEYCFKEFPEVK-YWTTF-NEIGPIGD (SEQ ID NO:37) |
| L18993 (P) | EALHSNGDFLNRENIEHFVNYAEFCFKEFSEVN-YWTTF-NEIGPIGD (SEQ ID NO:38) |
| M28357 (P) | EALHSNGDFLNRENIEHFIDYAAFCFEEFPEVN-YWTTF-NEIGPIGD (SEQ ID NO:39) |
| M34696 | GDFTGPSGWLSTRTVYEFARFSAYIAWKFDDLVDEYSTM-NEPNVVGG (SEQ ID NO:40) |
| X15950 | GDFTGPTGWLNSRTVYEFARFSAYVAWKLDDLASEYATM-NEPNVVWG (SEQ ID NO:41) |

FIG. 2

Reaction with 10% lactose.

|  | 0 µl | 0.1 µl | 0.2 µl | 0.4 µl | 0.8 µl | 1.5 µl | 3 µl | 6 µl |
|---|---|---|---|---|---|---|---|---|
| lactose | 112.38 | 105.87 | 101.35 | 92.52 | 75.56 | 51.82 | 34.04 | 30.08 |
| glucose | 0 | 1.52 | 2.85 | 6.11 | 11.53 | 20.66 | 30.16 | 36.92 |
| galactose | 0 | 0.19 | 0.30 | 0.66 | 1.30 | 2.16 | 3.80 | 5.58 |

Reaction with 20% lactose.

|  | 0 µl | 0.1 µl | 0.2 µl | 0.4 µl | 0.8 µl | 1.5 µl | 3 µl | 6 µl |
|---|---|---|---|---|---|---|---|---|
| lactose | 235.65 | 217.58 | 205.30 | 177.70 | 137.27 | 93.78 | 66.24 | 61.69 |
| glucose | 0 | 2.95 | 6.48 | 13.93 | 29.57 | 45.99 | 61.06 | 73.06 |
| galactose | 0 | 0.34 | 0.48 | 0.78 | 1.96 | 3.07 | 4.87 | 6.95 |

Reaction with 40% lactose.

|  | 0 µl | 0.1 µl | 0.2 µl | 0.4 µl | 0.8 µl | 1.5 µl | 3 µl | 6 µl |
|---|---|---|---|---|---|---|---|---|
| lactose | 426.47 | 395.16 | 370.29 | 308.07 | 224.08 | 174.88 | 136.73 | 121.29 |
| glucose | 0 | 7.96 | 17.51 | 37.96 | 63.42 | 93.99 | 123.99 | 144.27 |
| galactose | 0 | 0.65 | 0.97 | 1.48 | 2.94 | 4.11 | 6.84 | 8.89 |

Plot of reaction with 10% lactose.

SEQUENCE LISTING

```
<160> NUMBER OF SEQ ID NOS: 41

<210> SEQ ID NO 1
<211> LENGTH: 5509
<212> TYPE: DNA
<213> ORGANISM: Bifidobacterium bifidum
<220> FEATURE:
<221> NAME/KEY: CDS
<222> LOCATION: (212)..(5467)

<400> SEQUENCE: 1
atgcgttgcg ttgcgatttt tccggccctg tatgggggat acaggattgg cgatggcgac      60
acgccgtttt tgttaatggc atttacatga aatacaggta atgagatatc attctcatga     120
tcaccgtgtg gatatcgcat tggtgcgtat acactaacag caacagagcg gcgcggcagg     180
cgctcgtgga ttcaatgaag aaggaacgtt t atg gca gtt cgc aga ctt ggt        232
                                  Met Ala Val Arg Arg Leu Gly
                                    1               5 ggc cgc atc gtg gct ttc gcc gcc aca gtg gcc ttg tca ata ccg tta       280
Gly Arg Ile Val Ala Phe Ala Ala Thr Val Ala Leu Ser Ile Pro Leu
         10                  15                  20 ggg ttg tta aca aat tca gcg tgg gcg gtc gag gac gcc acc cga tcc       328
Gly Leu Leu Thr Asn Ser Ala Trp Ala Val Glu Asp Ala Thr Arg Ser
     25                  30                  35
```

```
gac tcc acc acg cag atg agc tcc acg ccg gag gtg gtc tac tcc agc      376
Asp Ser Thr Thr Gln Met Ser Ser Thr Pro Glu Val Val Tyr Ser Ser
 40                  45                  50                  55 gcc gtg gat tcc aag cag aat cgc acc tcg gat ttc gac gcc aac tgg      424
Ala Val Asp Ser Lys Gln Asn Arg Thr Ser Asp Phe Asp Ala Asn Trp
                 60                  65                  70 aag ttc atg ctg tcc gat tcc gtg cag gcg cag gat ccg gcg ttc gac      472
Lys Phe Met Leu Ser Asp Ser Val Gln Ala Gln Asp Pro Ala Phe Asp
             75                  80                  85 gat tcg gcc tgg cag cag gtc gac ctg ccg cat gac tac agc atc acg      520
Asp Ser Ala Trp Gln Gln Val Asp Leu Pro His Asp Tyr Ser Ile Thr
         90                  95                 100 cag aag tat tcg cag agc aac gag gcc gaa agc gca tac ctt ccc ggc      568
Gln Lys Tyr Ser Gln Ser Asn Glu Ala Glu Ser Ala Tyr Leu Pro Gly
    105                 110                 115 ggc acc ggc tgg tac cgc aag tcc ttc acc atc gac cgg gac ctc gcc      616
Gly Thr Gly Trp Tyr Arg Lys Ser Phe Thr Ile Asp Arg Asp Leu Ala
120                 125                 130                 135 ggc aag cgc atc gcc atc aac ttc gac ggc gtg tac atg aac gcc acc      664
Gly Lys Arg Ile Ala Ile Asn Phe Asp Gly Val Tyr Met Asn Ala Thr
                140                 145                 150 gtc tgg ttc aac ggc gtc aag ctc ggc acc cat ccg tac ggc tac tcg      712
Val Trp Phe Asn Gly Val Lys Leu Gly Thr His Pro Tyr Gly Tyr Ser
            155                 160                 165 ccg ttc tcc ttc gac ctg acc ggc aac gcc aag ttc ggt ggg gag aac      760
Pro Phe Ser Phe Asp Leu Thr Gly Asn Ala Lys Phe Gly Gly Glu Asn
        170                 175                 180 acc atc gtc gtc aag gtc gag aac agg ctg ccg tcc agc cgc tgg tac      808
Thr Ile Val Val Lys Val Glu Asn Arg Leu Pro Ser Ser Arg Trp Tyr
    185                 190                 195 tcc ggc tcc ggc atc tac cgc gac gtc acc ctc acc gtc acc gac ggc      856
Ser Gly Ser Gly Ile Tyr Arg Asp Val Thr Leu Thr Val Thr Asp Gly
200                 205                 210                 215 gtg cac gtc ggc aat aac ggc gtg gcc atc aag acc ccg agc ctc gcc      904
Val His Val Gly Asn Asn Gly Val Ala Ile Lys Thr Pro Ser Leu Ala
                220                 225                 230 acc caa aac ggc ggc gac gtg acg atg aac ctc acc acc aag gtc gcc      952
Thr Gln Asn Gly Gly Asp Val Thr Met Asn Leu Thr Thr Lys Val Ala
            235                 240                 245 aac gac acc gag gcc gcg gcg aac atc acc ctc aag cag acc gtg ttc     1000
Asn Asp Thr Glu Ala Ala Ala Asn Ile Thr Leu Lys Gln Thr Val Phe
        250                 255                 260 ccc aag gga ggc aag acc gac gcc gcc atc ggc acc gtc acc acc gca     1048
Pro Lys Gly Gly Lys Thr Asp Ala Ala Ile Gly Thr Val Thr Thr Ala
    265                 270                 275 tcc aag tcc atc gcg gcc ggt gcc agc gcg gac gtg acc tcc acg atc     1096
Ser Lys Ser Ile Ala Ala Gly Ala Ser Ala Asp Val Thr Ser Thr Ile
280                 285                 290                 295 acc gcc gct tcg ccc aag ctg tgg agc atc aag aac ccg aac ctg tac     1144
Thr Ala Ala Ser Pro Lys Leu Trp Ser Ile Lys Asn Pro Asn Leu Tyr
                300                 305                 310 acc gtg cgc acc gaa gtg ctc aac ggc ggc aag gtg ctc gac act tac     1192
Thr Val Arg Thr Glu Val Leu Asn Gly Gly Lys Val Leu Asp Thr Tyr
            315                 320                 325 gac acc gaa tat ggc ttc cgc tgg acc ggc ttc gat gcg acc agc ggt     1240
Asp Thr Glu Tyr Gly Phe Arg Trp Thr Gly Phe Asp Ala Thr Ser Gly
        330                 335                 340 ttc tcg ctc aac ggc gag aaa gtc aag ctc aag ggc gtc tca atg cat     1288
Phe Ser Leu Asn Gly Glu Lys Val Lys Leu Lys Gly Val Ser Met His
    345                 350                 355
```

-continued

```
cat gac cag gga tcg ctc ggc gcg gtc gcc aac cgc cgc gcc atc gag    1336
His Asp Gln Gly Ser Leu Gly Ala Val Ala Asn Arg Arg Ala Ile Glu
360             365             370             375 cgc cag gtc gag att ctc cag aag atg ggc gtc aac tcg atc cgc acc    1384
Arg Gln Val Glu Ile Leu Gln Lys Met Gly Val Asn Ser Ile Arg Thr
        380             385             390 acg cac aac ccc gca gcc aag gcg ctg att gac gtc tgc aac gag aag    1432
Thr His Asn Pro Ala Ala Lys Ala Leu Ile Asp Val Cys Asn Glu Lys
            395             400             405 ggc gtc ctc gtg gtc gaa gag gtc ttc gac atg tgg aac cgg tcg aag    1480
Gly Val Leu Val Val Glu Glu Val Phe Asp Met Trp Asn Arg Ser Lys
                410             415             420 aac ggc aac acc gag gat tac ggc aag tgg ttc ggc cag gcc atc gcc    1528
Asn Gly Asn Thr Glu Asp Tyr Gly Lys Trp Phe Gly Gln Ala Ile Ala
425             430             435 ggt gac aac gcc gtc ctg ggt ggc gac aag gac gag acc tgg gcc aag    1576
Gly Asp Asn Ala Val Leu Gly Gly Asp Lys Asp Glu Thr Trp Ala Lys
440             445             450             455 ttc gac ctg acc agc acc atc aac cgt gac agg aac gcc ccg tcc gtc    1624
Phe Asp Leu Thr Ser Thr Ile Asn Arg Asp Arg Asn Ala Pro Ser Val
        460             465             470 atc atg tgg tcg ctc ggc aac gag atg atg gaa ggc atc agc ggc agc    1672
Ile Met Trp Ser Leu Gly Asn Glu Met Met Glu Gly Ile Ser Gly Ser
            475             480             485 gtc tcg ggc ttc ccg gct acc tcc gcc aag ctg gtc gca tgg acg aag    1720
Val Ser Gly Phe Pro Ala Thr Ser Ala Lys Leu Val Ala Trp Thr Lys
                490             495             500 gcc gcg gac agc acc cgc ccg atg acc tac ggc gac aac aag atc aag    1768
Ala Ala Asp Ser Thr Arg Pro Met Thr Tyr Gly Asp Asn Lys Ile Lys
505             510             515 gcc aac tgg aac gag tcg aac acc atg ggc gac aac ctg acc gcc aac    1816
Ala Asn Trp Asn Glu Ser Asn Thr Met Gly Asp Asn Leu Thr Ala Asn
520             525             530             535 ggc ggc gtg gtc ggc acc aac tac tcc gac ggc gcg aac tac gac aag    1864
Gly Gly Val Val Gly Thr Asn Tyr Ser Asp Gly Ala Asn Tyr Asp Lys
        540             545             550 atc cgc acg acc cac ccc tca tgg gcc atc tat ggt tcc gag acg gcg    1912
Ile Arg Thr Thr His Pro Ser Trp Ala Ile Tyr Gly Ser Glu Thr Ala
            555             560             565 tcc gcc atc aac agc cga ggc atc tac aac cgc acc acc ggc ggc gcc    1960
Ser Ala Ile Asn Ser Arg Gly Ile Tyr Asn Arg Thr Thr Gly Gly Ala
                570             575             580 cag tca agc gac aag cag ctg acc agc tat gac aat tcc gca gtc ggc    2008
Gln Ser Ser Asp Lys Gln Leu Thr Ser Tyr Asp Asn Ser Ala Val Gly
585             590             595 tgg ggc gcc gtc gcc agc tcc gcc tgg tac gac gtg gtc cag cgc gat    2056
Trp Gly Ala Val Ala Ser Ser Ala Trp Tyr Asp Val Val Gln Arg Asp
600             605             610             615 ttc gtc gcc ggc aca tac gtg tgg acc ggc ttc gac tac ctc ggc gaa    2104
Phe Val Ala Gly Thr Tyr Val Trp Thr Gly Phe Asp Tyr Leu Gly Glu
        620             625             630 ccc acc ccg tgg aac ggc acc ggc tcc ggc gcc gtg ggc tcc ttg gcc    2152
Pro Thr Pro Trp Asn Gly Thr Gly Ser Gly Ala Val Gly Ser Leu Ala
            635             640             645 gtc gcc gaa gaa ctc gta ctt cgg cat cgt cga cac cgc agg ctt ccc    2200
Val Ala Glu Glu Leu Val Leu Arg His Arg Arg His Arg Arg Leu Pro
                650             655             660 gaa gac acc tat tac ttc tat cag agc cag tgg aac gac gac gtg cac    2248
Glu Asp Thr Tyr Tyr Phe Tyr Gln Ser Gln Trp Asn Asp Asp Val His
```

-continued

```
          665                 670                 675
acg ctg cac atc ctc ccc gca tgg aac gag aac gtc gtc gcc aag ggc      2296
Thr Leu His Ile Leu Pro Ala Trp Asn Glu Asn Val Val Ala Lys Gly
680                 685                 690                 695 tcc ggc aac aac gtg ccg gtc gtc tac acc gac gcg gcc aag gtc          2344
Ser Gly Asn Asn Val Pro Val Val Tyr Thr Asp Ala Ala Lys Val
                700                 705                 710 aag ctg tac ttc aca ccg aag ggc agt acc gaa aag cga ctg atc gga      2392
Lys Leu Tyr Phe Thr Pro Lys Gly Ser Thr Glu Lys Arg Leu Ile Gly
                715                 720                 725 gag aag tcc ttc acc aag aag acc acc gcg gcc gga tac acc tat cag      2440
Glu Lys Ser Phe Thr Lys Lys Thr Thr Ala Ala Gly Tyr Thr Tyr Gln
            730                 735                 740 gtc tac gag ggc tcc gac aag gac tcc acc gcc cac aag aac atg tac      2488
Val Tyr Glu Gly Ser Asp Lys Asp Ser Thr Ala His Lys Asn Met Tyr
745                 750                 755 ctg acc tgg aac gtg ccg tgg gcc gag ggc acc atc tcc gcc gaa gca      2536
Leu Thr Trp Asn Val Pro Trp Ala Glu Gly Thr Ile Ser Ala Glu Ala
760                 765                 770                 775 tac gac gag aac aac agg ctg atc ccc gag ggg tcc acc gag ggc aac      2584
Tyr Asp Glu Asn Asn Arg Leu Ile Pro Glu Gly Ser Thr Glu Gly Asn
                780                 785                 790 gcg tcg gtg acc acc acc ggc aag gcc gcg aag ctt aaa gcc gat gcc      2632
Ala Ser Val Thr Thr Thr Gly Lys Ala Ala Lys Leu Lys Ala Asp Ala
                795                 800                 805 gac cgc aag acg atc acc gcg gac ggc aag gac ctg tcg tac atc gag      2680
Asp Arg Lys Thr Ile Thr Ala Asp Gly Lys Asp Leu Ser Tyr Ile Glu
            810                 815                 820 gtc gac gtg acc gac gcc aac ggc cat atc gtc ccc gat gcc gcc aac      2728
Val Asp Val Thr Asp Ala Asn Gly His Ile Val Pro Asp Ala Ala Asn
825                 830                 835 cgc gtc acc ttc gac gtc aag ggc gcc ggc aaa ctg gtc ggc gtc gac      2776
Arg Val Thr Phe Asp Val Lys Gly Ala Gly Lys Leu Val Gly Val Asp
840                 845                 850                 855 aac ggc agc tcg ccg gat cac gac tcc tat cag gcc gac aac cgc aag      2824
Asn Gly Ser Ser Pro Asp His Asp Ser Tyr Gln Ala Asp Asn Arg Lys
                860                 865                 870 gcg ttc agc ggc aag gtg ctc gcc atc gtc cag tcc acc aag gag gcg      2872
Ala Phe Ser Gly Lys Val Leu Ala Ile Val Gln Ser Thr Lys Glu Ala
                875                 880                 885 ggc gag atc acc gtc acc gcc aag gcc gac ggt ctg caa tca tcc aca      2920
Gly Glu Ile Thr Val Thr Ala Lys Ala Asp Gly Leu Gln Ser Ser Thr
            890                 895                 900 gtg aag atc gcc acc acc gcc gtc ccc ggc acc agc acc gag aag acg      2968
Val Lys Ile Ala Thr Thr Ala Val Pro Gly Thr Ser Thr Glu Lys Thr
            905                 910                 915 gtc cgc agc ttc tac tac tcg cgc aac tac tac gtc aag acc ggc aac      3016
Val Arg Ser Phe Tyr Tyr Ser Arg Asn Tyr Tyr Val Lys Thr Gly Asn
920                 925                 930                 935 aag ccg att ctg ccg agt gat gtc gag gtg cgc tac tcc gac ggc acg      3064
Lys Pro Ile Leu Pro Ser Asp Val Glu Val Arg Tyr Ser Asp Gly Thr
                940                 945                 950 tcg gac cgt cag aac gtc aca tgg gac gca gtc agc gac gac cag atc      3112
Ser Asp Arg Gln Asn Val Thr Trp Asp Ala Val Ser Asp Asp Gln Ile
                955                 960                 965 gcc aag gcc ggt tcg ttc agc gtg gcc ggc acg gtc gcc ggg cag aag      3160
Ala Lys Ala Gly Ser Phe Ser Val Ala Gly Thr Val Ala Gly Gln Lys
                970                 975                 980 atc tcc gtg cgc gtg acg atg atc gac gag atc ggt gcg ctg ctc aac      3208
```

```
                Ile Ser Val Arg Val Thr Met Ile Asp Glu Ile Gly Ala Leu Leu Asn
                    985                 990                 995 tat tcg gcc agc aca ccg gtc ggc acg ccc gcc gtg ctg cct ggc tcg          3256
Tyr Ser Ala Ser Thr Pro Val Gly Thr Pro Ala Val Leu Pro Gly Ser
1000                1005                1010                1015 cgt ccg gcc gtg ctg ccc gac ggc acc gtg acc agc gcg aac ttc gcc          3304
Arg Pro Ala Val Leu Pro Asp Gly Thr Val Thr Ser Ala Asn Phe Ala
            1020                1025                1030 gtc cac tgg acc aag ccc gcc gac acc gtg tac aac acg gcc ggc acc          3352
Val His Trp Thr Lys Pro Ala Asp Thr Val Tyr Asn Thr Ala Gly Thr
                1035                1040                1045 gtc aag gtc ccc ggc acc gcc acc gtc ttc ggc aag gag ttc aag gtc          3400
Val Lys Val Pro Gly Thr Ala Thr Val Phe Gly Lys Glu Phe Lys Val
1050                1055                1060 acc gcg acg att cgc gtg cag cgg tcg cag gtc acc atc ggc agc agc          3448
Thr Ala Thr Ile Arg Val Gln Arg Ser Gln Val Thr Ile Gly Ser Ser
    1065                1070                1075 gtc tcc ggc aat gcg ctg cgc ctg act cag aac atc ccc gcc gac aag          3496
Val Ser Gly Asn Ala Leu Arg Leu Thr Gln Asn Ile Pro Ala Asp Lys
1080                1085                1090                1095 cag tcc gac acg ctg gac gcc atc aag gac ggc tcc acg acc gtc gac          3544
Gln Ser Asp Thr Leu Asp Ala Ile Lys Asp Gly Ser Thr Thr Val Asp
            1100                1105                1110 gcc aat acc ggc ggc ggc gcg aac ccg tca gca tgg acc aac tgg gcg          3592
Ala Asn Thr Gly Gly Gly Ala Asn Pro Ser Ala Trp Thr Asn Trp Ala
                1115                1120                1125 tac tcg aag gcc ggc cac aac acc gcc gag atc acc ttc gag tac gcg          3640
Tyr Ser Lys Ala Gly His Asn Thr Ala Glu Ile Thr Phe Glu Tyr Ala
1130                1135                1140 acc gag cag cag ctc ggc cag att gtc atg tac ttc ttc cgc gac agc          3688
Thr Glu Gln Gln Leu Gly Gln Ile Val Met Tyr Phe Phe Arg Asp Ser
    1145                1150                1155 aac gcg gtg agg ttc ccc gac gcc ggc aag acg aag atc cag atc tcc          3736
Asn Ala Val Arg Phe Pro Asp Ala Gly Lys Thr Lys Ile Gln Ile Ser
1160                1165                1170                1175 gcg gac ggc aag aac tgg acg gat ctc gct gcc acg gag acc atc gcg          3784
Ala Asp Gly Lys Asn Trp Thr Asp Leu Ala Ala Thr Glu Thr Ile Ala
            1180                1185                1190 gcc cag gag tcg tcc gac cga gtc aag ccg tac acc tat gac ttc gct          3832
Ala Gln Glu Ser Ser Asp Arg Val Lys Pro Tyr Thr Tyr Asp Phe Ala
                1195                1200                1205 ccg gtg gga gcc acg ttc gtc aag gtc acg gtc acc aac gcc gac acc          3880
Pro Val Gly Ala Thr Phe Val Lys Val Thr Val Thr Asn Ala Asp Thr
1210                1215                1220 aca acc ccc agc ggc gtg gtc tgc gcc ggc ctg acc gag atc gag ctg          3928
Thr Thr Pro Ser Gly Val Val Cys Ala Gly Leu Thr Glu Ile Glu Leu
    1225                1230                1235 aag acc gcg acc agc aag ttc gtc acg aac acg tcc gcc gcg ctc tcg          3976
Lys Thr Ala Thr Ser Lys Phe Val Thr Asn Thr Ser Ala Ala Leu Ser
1240                1245                1250                1255 tcg ctg aca gtg aac ggc acg aag gtc tcc gac tcc gtg ctc gcc gcc          4024
Ser Leu Thr Val Asn Gly Thr Lys Val Ser Asp Ser Val Leu Ala Ala
            1260                1265                1270 ggc tcc tac aac acg ccc gcg atc atc gcg gac gtc aaa gcc gag ggc          4072
Gly Ser Tyr Asn Thr Pro Ala Ile Ile Ala Asp Val Lys Ala Glu Gly
                1275                1280                1285 gaa ggc aac gcc agc gtc acc gtg ctg ccc gcg cac gac aac gtg atc          4120
Glu Gly Asn Ala Ser Val Thr Val Leu Pro Ala His Asp Asn Val Ile
1290                1295                1300
```

-continued

```
cgc gtg atc acc gag tcc gag gac cac gtc acg cgc aag acc ttc acc         4168
Arg Val Ile Thr Glu Ser Glu Asp His Val Thr Arg Lys Thr Phe Thr
    1305                1310                1315 atc aac ctg ggc acg gag cag gaa ttc ccc gca gac tcc gat gaa cgc         4216
Ile Asn Leu Gly Thr Glu Gln Glu Phe Pro Ala Asp Ser Asp Glu Arg
1320                1325                1330                1335 gac tac ccg gcc gcc gac atg acg gtc acc gtg ggc agc gaa cag acg         4264
Asp Tyr Pro Ala Ala Asp Met Thr Val Thr Val Gly Ser Glu Gln Thr
            1340                1345                1350 tcc ggc acc gcg acc gaa ggc ccg aag aaa ttc gcg gtc gac ggc aac         4312
Ser Gly Thr Ala Thr Glu Gly Pro Lys Lys Phe Ala Val Asp Gly Asn
        1355                1360                1365 acc agc acg tac tgg cat tcc aac tgg acg ccc acc acc gtg aac gac         4360
Thr Ser Thr Tyr Trp His Ser Asn Trp Thr Pro Thr Thr Val Asn Asp
    1370                1375                1380 ctg tgg atc gcc ttc gag ctc cag aaa ccc acc aag ctc gac gcg ctg         4408
Leu Trp Ile Ala Phe Glu Leu Gln Lys Pro Thr Lys Leu Asp Ala Leu
    1385                1390                1395 cgc tac ctg ccg cgc ccc gcg ggc agc aag aac ggc tcc gtc acc gaa         4456
Arg Tyr Leu Pro Arg Pro Ala Gly Ser Lys Asn Gly Ser Val Thr Glu
1400                1405                1410                1415 tac aag gtt cag gtc agc gat gac ggc acc aac tgg acc gac gcg ggc         4504
Tyr Lys Val Gln Val Ser Asp Asp Gly Thr Asn Trp Thr Asp Ala Gly
            1420                1425                1430 tcc ggc aca tgg acc acc gat tac ggc tgg aag ctc gcc gag ttc aat         4552
Ser Gly Thr Trp Thr Thr Asp Tyr Gly Trp Lys Leu Ala Glu Phe Asn
        1435                1440                1445 cag ccg gtg acc acc aag cac gtg cgg ctc aag gcc gtc cac acc tat         4600
Gln Pro Val Thr Thr Lys His Val Arg Leu Lys Ala Val His Thr Tyr
    1450                1455                1460 gcg gat tcc ggc aac gac aag ttc atg tcc gcc tcc gaa atc cgc ctg         4648
Ala Asp Ser Gly Asn Asp Lys Phe Met Ser Ala Ser Glu Ile Arg Leu
    1465                1470                1475 cgc aag gcc gtc gac acc acc gac atc agc ggc gcg acc gtg acc gtg         4696
Arg Lys Ala Val Asp Thr Thr Asp Ile Ser Gly Ala Thr Val Thr Val
1480                1485                1490                1495 ccc gcc aag ctg acc gtc gac cgg gtg gac gcc gac cat ccc gcc acc         4744
Pro Ala Lys Leu Thr Val Asp Arg Val Asp Ala Asp His Pro Ala Thr
            1500                1505                1510 ttc gcc acg aag gac gtg acg gtg acg ttg ggc gac gcc acg ctg cgc         4792
Phe Ala Thr Lys Asp Val Thr Val Thr Leu Gly Asp Ala Thr Leu Arg
        1515                1520                1525 tac ggc gtg gac tac ctg ctc gac tac gcg ggc aac acc gcc gtc ggc         4840
Tyr Gly Val Asp Tyr Leu Leu Asp Tyr Ala Gly Asn Thr Ala Val Gly
    1530                1535                1540 aag gcc acg gtg acc gtg cgc ggc atc gac aag tac tcc ggc acc gtc         4888
Lys Ala Thr Val Thr Val Arg Gly Ile Asp Lys Tyr Ser Gly Thr Val
    1545                1550                1555 gcc aag acg ttc acc atc gaa ctg aag aac gcc ccg gcg ccg gaa ccg         4936
Ala Lys Thr Phe Thr Ile Glu Leu Lys Asn Ala Pro Ala Pro Glu Pro
1560                1565                1570                1575 acg ctg acc tcg gtg agc gtc aag acc aag cct tcc aag ctg acc tat         4984
Thr Leu Thr Ser Val Ser Val Lys Thr Lys Pro Ser Lys Leu Thr Tyr
            1580                1585                1590 gtg gtc ggc gac gcg ttc gac ccg gca gga ctg gtg ctg cag cac gac         5032
Val Val Gly Asp Ala Phe Asp Pro Ala Gly Leu Val Leu Gln His Asp
        1595                1600                1605 aga cag gcc gat cgc ccc cca cag cca ctt gtt gga gaa cag gcc gac         5080
Arg Gln Ala Asp Arg Pro Pro Gln Pro Leu Val Gly Glu Gln Ala Asp
    1610                1615                1620
```

-continued

```
gaa cgc gga ctg acg tgc gga acg cga tgc gat cgc gtt gaa cag ctg      5128
Glu Arg Gly Leu Thr Cys Gly Thr Arg Cys Asp Arg Val Glu Gln Leu
    1625                1630                1635 cgc aaa cac gag aat cgt gaa gcc cat cgt acg ggc ctc gat cat ctg      5176
Arg Lys His Glu Asn Arg Glu Ala His Arg Thr Gly Leu Asp His Leu
1640                1645                1650                1655 gaa ttc gtg ggt gcc gcc gat gga gcg gtc ggt gaa cag gcc acc ttc      5224
Glu Phe Val Gly Ala Ala Asp Gly Ala Val Gly Glu Gln Ala Thr Phe
                1660                1665                1670 aag gtg cat gtc cat gcc gat caa ggt gac ggc cgc cat gat gat gcc      5272
Lys Val His Val His Ala Asp Gln Gly Asp Gly Arg His Asp Asp Ala
            1675                1680                1685 gat gaa cgc gat atc gat cca cat gtc cct gtc gat cac gcg gtc ggt      5320
Asp Glu Arg Asp Ile Asp Pro His Val Pro Val Asp His Ala Val Gly
        1690                1695                1700 gag ctt gcg cgg gct gcg tgc cat cac gtc atc ggt ctg cgg gtc gac      5368
Glu Leu Ala Arg Ala Ala Cys His His Val Ile Gly Leu Arg Val Asp
    1705                1710                1715 acc cat cgc ctc aag gca tcc ggc ttc cag atc ccc gcc gac gac atg      5416
Thr His Arg Leu Lys Ala Ser Gly Phe Gln Ile Pro Ala Asp Asp Met
1720                1725                1730                1735 gcc gag atc gac cgc atc acc ggc ttc cac cgc ttc gag cgc cac gtc      5464
Ala Glu Ile Asp Arg Ile Thr Gly Phe His Arg Phe Glu Arg His Val
                1740                1745                1750 ggc tgacgtgatt gggcttcccc gctgtctggt gccggctcgc ga                   5509
Gly
```

<210> SEQ ID NO 2
<211> LENGTH: 1752
<212> TYPE: PRT
<213> ORGANISM: Bifidobacterium bifidum

<400> SEQUENCE: 2

```
Met Ala Val Arg Arg Leu Gly Gly Arg Ile Val Ala Phe Ala Ala Thr
  1               5                  10                  15

Val Ala Leu Ser Ile Pro Leu Gly Leu Leu Thr Asn Ser Ala Trp Ala
                 20                  25                  30

Val Glu Asp Ala Thr Arg Ser Asp Ser Thr Thr Gln Met Ser Ser Thr
             35                  40                  45

Pro Glu Val Val Tyr Ser Ser Ala Val Asp Ser Lys Gln Asn Arg Thr
         50                  55                  60

Ser Asp Phe Asp Ala Asn Trp Lys Phe Met Leu Ser Asp Ser Val Gln
 65                  70                  75                  80

Ala Gln Asp Pro Ala Phe Asp Asp Ser Ala Trp Gln Gln Val Asp Leu
                 85                  90                  95

Pro His Asp Tyr Ser Ile Thr Gln Lys Tyr Ser Gln Ser Asn Glu Ala
            100                 105                 110

Glu Ser Ala Tyr Leu Pro Gly Gly Thr Gly Trp Tyr Arg Lys Ser Phe
        115                 120                 125

Thr Ile Asp Arg Asp Leu Ala Gly Lys Arg Ile Ala Ile Asn Phe Asp
130                 135                 140

Gly Val Tyr Met Asn Ala Thr Val Trp Phe Asn Gly Val Lys Leu Gly
145                 150                 155                 160

Thr His Pro Tyr Gly Tyr Ser Pro Phe Ser Phe Asp Leu Thr Gly Asn
                165                 170                 175

Ala Lys Phe Gly Gly Glu Asn Thr Ile Val Val Lys Val Glu Asn Arg
            180                 185                 190
```

-continued

```
Leu Pro Ser Ser Arg Trp Tyr Ser Gly Ser Gly Ile Tyr Arg Asp Val
        195                 200                 205
Thr Leu Thr Val Thr Asp Gly Val His Val Gly Asn Asn Gly Val Ala
    210                 215                 220
Ile Lys Thr Pro Ser Leu Ala Thr Gln Asn Gly Gly Asp Val Thr Met
225                 230                 235                 240
Asn Leu Thr Thr Lys Val Ala Asn Asp Thr Glu Ala Ala Ala Asn Ile
            245                 250                 255
Thr Leu Lys Gln Thr Val Phe Pro Lys Gly Gly Lys Thr Asp Ala Ala
            260                 265                 270
Ile Gly Thr Val Thr Thr Ala Ser Lys Ser Ile Ala Ala Gly Ala Ser
        275                 280                 285
Ala Asp Val Thr Ser Thr Ile Thr Ala Ala Ser Pro Lys Leu Trp Ser
    290                 295                 300
Ile Lys Asn Pro Asn Leu Tyr Thr Val Arg Thr Glu Val Leu Asn Gly
305                 310                 315                 320
Gly Lys Val Leu Asp Thr Tyr Asp Thr Glu Tyr Gly Phe Arg Trp Thr
            325                 330                 335
Gly Phe Asp Ala Thr Ser Gly Phe Ser Leu Asn Gly Glu Lys Val Lys
            340                 345                 350
Leu Lys Gly Val Ser Met His His Asp Gln Gly Ser Leu Gly Ala Val
        355                 360                 365
Ala Asn Arg Arg Ala Ile Glu Arg Gln Val Glu Ile Leu Gln Lys Met
    370                 375                 380
Gly Val Asn Ser Ile Arg Thr Thr His Asn Pro Ala Ala Lys Ala Leu
385                 390                 395                 400
Ile Asp Val Cys Asn Glu Lys Gly Val Leu Val Val Glu Glu Val Phe
            405                 410                 415
Asp Met Trp Asn Arg Ser Lys Asn Gly Asn Thr Glu Asp Tyr Gly Lys
            420                 425                 430
Trp Phe Gly Gln Ala Ile Ala Gly Asp Asn Ala Val Leu Gly Gly Asp
        435                 440                 445
Lys Asp Glu Thr Trp Ala Lys Phe Asp Leu Thr Ser Thr Ile Asn Arg
    450                 455                 460
Asp Arg Asn Ala Pro Ser Val Ile Met Trp Ser Leu Gly Asn Glu Met
465                 470                 475                 480
Met Glu Gly Ile Ser Gly Ser Val Ser Gly Phe Pro Ala Thr Ser Ala
            485                 490                 495
Lys Leu Val Ala Trp Thr Lys Ala Ala Asp Ser Thr Arg Pro Met Thr
            500                 505                 510
Tyr Gly Asp Asn Lys Ile Lys Ala Asn Trp Asn Glu Ser Asn Thr Met
        515                 520                 525
Gly Asp Asn Leu Thr Ala Asn Gly Val Val Gly Thr Asn Tyr Ser
    530                 535                 540
Asp Gly Ala Asn Tyr Asp Lys Ile Arg Thr Thr His Pro Ser Trp Ala
545                 550                 555                 560
Ile Tyr Gly Ser Glu Thr Ala Ser Ala Ile Asn Ser Arg Gly Ile Tyr
            565                 570                 575
Asn Arg Thr Thr Gly Gly Ala Gln Ser Ser Asp Lys Gln Leu Thr Ser
            580                 585                 590
Tyr Asp Asn Ser Ala Val Gly Trp Gly Ala Val Ala Ser Ser Ala Trp
        595                 600                 605
```

-continued

```
Tyr Asp Val Val Gln Arg Asp Phe Val Ala Gly Thr Tyr Val Trp Thr
    610                 615                 620
Gly Phe Asp Tyr Leu Gly Glu Pro Thr Pro Trp Asn Gly Thr Gly Ser
625                 630                 635                 640
Gly Ala Val Gly Ser Leu Ala Val Ala Glu Glu Leu Val Leu Arg His
                645                 650                 655
Arg Arg His Arg Arg Leu Pro Glu Asp Thr Tyr Tyr Phe Tyr Gln Ser
            660                 665                 670
Gln Trp Asn Asp Asp Val His Thr Leu His Ile Leu Pro Ala Trp Asn
        675                 680                 685
Glu Asn Val Val Ala Lys Gly Ser Gly Asn Asn Val Pro Val Val Val
    690                 695                 700
Tyr Thr Asp Ala Ala Lys Val Lys Leu Tyr Phe Thr Pro Lys Gly Ser
705                 710                 715                 720
Thr Glu Lys Arg Leu Ile Gly Glu Lys Ser Phe Thr Lys Lys Thr Thr
                725                 730                 735
Ala Ala Gly Tyr Thr Tyr Gln Val Tyr Glu Gly Ser Asp Lys Asp Ser
            740                 745                 750
Thr Ala His Lys Asn Met Tyr Leu Thr Trp Asn Val Pro Trp Ala Glu
        755                 760                 765
Gly Thr Ile Ser Ala Glu Ala Tyr Asp Glu Asn Asn Arg Leu Ile Pro
    770                 775                 780
Glu Gly Ser Thr Glu Gly Asn Ala Ser Val Thr Thr Thr Gly Lys Ala
785                 790                 795                 800
Ala Lys Leu Lys Ala Asp Ala Asp Arg Lys Thr Ile Thr Ala Asp Gly
                805                 810                 815
Lys Asp Leu Ser Tyr Ile Glu Val Asp Val Thr Asp Ala Asn Gly His
            820                 825                 830
Ile Val Pro Asp Ala Ala Asn Arg Val Thr Phe Asp Val Lys Gly Ala
        835                 840                 845
Gly Lys Leu Val Gly Val Asp Asn Gly Ser Ser Pro Asp His Asp Ser
    850                 855                 860
Tyr Gln Ala Asp Asn Arg Lys Ala Phe Ser Gly Lys Val Leu Ala Ile
865                 870                 875                 880
Val Gln Ser Thr Lys Glu Ala Gly Glu Ile Thr Val Thr Ala Lys Ala
                885                 890                 895
Asp Gly Leu Gln Ser Ser Thr Val Lys Ile Ala Thr Thr Ala Val Pro
            900                 905                 910
Gly Thr Ser Thr Glu Lys Thr Val Arg Ser Phe Tyr Tyr Ser Arg Asn
        915                 920                 925
Tyr Tyr Val Lys Thr Gly Asn Lys Pro Ile Leu Pro Ser Asp Val Glu
    930                 935                 940
Val Arg Tyr Ser Asp Gly Thr Ser Asp Arg Gln Asn Val Thr Trp Asp
945                 950                 955                 960
Ala Val Ser Asp Asp Gln Ile Ala Lys Ala Gly Ser Phe Ser Val Ala
                965                 970                 975
Gly Thr Val Ala Gly Gln Lys Ile Ser Val Arg Val Thr Met Ile Asp
            980                 985                 990
Glu Ile Gly Ala Leu Leu Asn Tyr Ser Ala Ser Thr Pro Val Gly Thr
        995                 1000                1005
Pro Ala Val Leu Pro Gly Ser Arg Pro Ala Val Leu Pro Asp Gly Thr
    1010                1015                1020
Val Thr Ser Ala Asn Phe Ala Val His Trp Thr Lys Pro Ala Asp Thr
```

-continued

```
            1025            1030            1035            1040
Val Tyr Asn Thr Ala Gly Thr Val Lys Val Pro Gly Thr Ala Thr Val
                    1045            1050            1055
Phe Gly Lys Glu Phe Lys Val Thr Ala Thr Ile Arg Val Gln Arg Ser
            1060            1065            1070
Gln Val Thr Ile Gly Ser Ser Val Ser Gly Asn Ala Leu Arg Leu Thr
        1075            1080            1085
Gln Asn Ile Pro Ala Asp Lys Gln Ser Asp Thr Leu Asp Ala Ile Lys
    1090            1095            1100
Asp Gly Ser Thr Thr Val Asp Ala Asn Thr Gly Gly Gly Ala Asn Pro
1105            1110            1115            1120
Ser Ala Trp Thr Asn Trp Ala Tyr Ser Lys Ala Gly His Asn Thr Ala
            1125            1130            1135
Glu Ile Thr Phe Glu Tyr Ala Thr Glu Gln Gln Leu Gly Gln Ile Val
                    1140            1145            1150
Met Tyr Phe Phe Arg Asp Ser Asn Ala Val Arg Phe Pro Asp Ala Gly
            1155            1160            1165
Lys Thr Lys Ile Gln Ile Ser Ala Asp Gly Lys Asn Trp Thr Asp Leu
    1170            1175            1180
Ala Ala Thr Glu Thr Ile Ala Ala Gln Glu Ser Ser Asp Arg Val Lys
1185            1190            1195            1200
Pro Tyr Thr Tyr Asp Phe Ala Pro Val Gly Ala Thr Phe Val Lys Val
            1205            1210            1215
Thr Val Thr Asn Ala Asp Thr Thr Pro Ser Gly Val Val Cys Ala
            1220            1225            1230
Gly Leu Thr Glu Ile Glu Leu Lys Thr Ala Thr Ser Lys Phe Val Thr
    1235            1240            1245
Asn Thr Ser Ala Ala Leu Ser Ser Leu Thr Val Asn Gly Thr Lys Val
    1250            1255            1260
Ser Asp Ser Val Leu Ala Ala Gly Ser Tyr Asn Thr Pro Ala Ile Ile
1265            1270            1275            1280
Ala Asp Val Lys Ala Glu Gly Glu Gly Asn Ala Ser Val Thr Val Leu
            1285            1290            1295
Pro Ala His Asp Asn Val Ile Arg Val Ile Thr Glu Ser Glu Asp His
            1300            1305            1310
Val Thr Arg Lys Thr Phe Thr Ile Asn Leu Gly Thr Glu Gln Glu Phe
        1315            1320            1325
Pro Ala Asp Ser Asp Glu Arg Asp Tyr Pro Ala Ala Asp Met Thr Val
    1330            1335            1340
Thr Val Gly Ser Glu Gln Thr Ser Gly Thr Ala Thr Glu Gly Pro Lys
1345            1350            1355            1360
Lys Phe Ala Val Asp Gly Asn Thr Ser Thr Tyr Trp His Ser Asn Trp
            1365            1370            1375
Thr Pro Thr Thr Val Asn Asp Leu Trp Ile Ala Phe Glu Leu Gln Lys
            1380            1385            1390
Pro Thr Lys Leu Asp Ala Leu Arg Tyr Leu Pro Arg Pro Ala Gly Ser
            1395            1400            1405
Lys Asn Gly Ser Val Thr Glu Tyr Lys Val Gln Val Ser Asp Gly
        1410            1415            1420
Thr Asn Trp Thr Asp Ala Gly Ser Gly Thr Trp Thr Thr Asp Tyr Gly
    1425            1430            1435            1440
Trp Lys Leu Ala Glu Phe Asn Gln Pro Val Thr Thr Lys His Val Arg
            1445            1450            1455
```

-continued

```
Leu Lys Ala Val His Thr Tyr Ala Asp Ser Gly Asn Asp Lys Phe Met
        1460                1465                1470
Ser Ala Ser Glu Ile Arg Leu Arg Lys Ala Val Asp Thr Thr Asp Ile
    1475                1480                1485
Ser Gly Ala Thr Val Thr Val Pro Ala Lys Leu Thr Val Asp Arg Val
    1490                1495                1500
Asp Ala Asp His Pro Ala Thr Phe Ala Thr Lys Asp Val Thr Val Thr
1505                1510                1515                1520
Leu Gly Asp Ala Thr Leu Arg Tyr Gly Val Asp Tyr Leu Leu Asp Tyr
            1525                1530                1535
Ala Gly Asn Thr Ala Val Gly Lys Ala Thr Val Thr Val Arg Gly Ile
        1540                1545                1550
Asp Lys Tyr Ser Gly Thr Val Ala Lys Thr Phe Thr Ile Glu Leu Lys
    1555                1560                1565
Asn Ala Pro Ala Pro Glu Pro Thr Leu Thr Ser Val Ser Val Lys Thr
    1570                1575                1580
Lys Pro Ser Lys Leu Thr Tyr Val Val Gly Asp Ala Phe Asp Pro Ala
1585                1590                1595                1600
Gly Leu Val Leu Gln His Asp Arg Gln Ala Asp Arg Pro Pro Gln Pro
            1605                1610                1615
Leu Val Gly Glu Gln Ala Asp Glu Arg Gly Leu Thr Cys Gly Thr Arg
        1620                1625                1630
Cys Asp Arg Val Glu Gln Leu Arg Lys His Glu Asn Arg Glu Ala His
    1635                1640                1645
Arg Thr Gly Leu Asp His Leu Glu Phe Val Gly Ala Ala Asp Gly Ala
    1650                1655                1660
Val Gly Glu Gln Ala Thr Phe Lys Val His Val His Ala Asp Gln Gly
1665                1670                1675                1680
Asp Gly Arg His Asp Asp Ala Asp Glu Arg Asp Ile Asp Pro His Val
            1685                1690                1695
Pro Val Asp His Ala Val Gly Glu Leu Ala Arg Ala Ala Cys His His
        1700                1705                1710
Val Ile Gly Leu Arg Val Asp Thr His Arg Leu Lys Ala Ser Gly Phe
    1715                1720                1725
Gln Ile Pro Ala Asp Asp Met Ala Glu Ile Asp Arg Ile Thr Gly Phe
    1730                1735                1740
His Arg Phe Glu Arg His Val Gly
1745                1750

<210> SEQ ID NO 3
<211> LENGTH: 4810
<212> TYPE: DNA
<213> ORGANISM: Bifidobacterium bifidum

<400> SEQUENCE: 3
atggcagttc gcagacttgg tggccgcatc gtggctttcg ccgccacagt ggccttgtca      60
ataccgttag ggttgttaac aaattcagcg tgggcggtcg aggacgccac ccgatccgac     120
tccaccacgc agatgagctc cacgccggag gtggtctact ccagcgccgt ggattccaag     180
cagaatcgca cctcggattt cgacgccaac tggaagttca tgctgtccga ttccgtgcag     240
gcgcaggatc cggcgttcga cgattcggcc tggcagcagg tcgacctgcc gcatgactac     300
agcatcacgc agaagtattc gcagagcaac gaggccgaaa gcgcatacct tcccggcggc     360
accggctggt accgcaagtc cttcaccatc gaccgggacc tcgccggcaa gcgcatcgcc     420
```

-continued

| | | | | | |
|---|---|---|---|---|---|
| atcaacttcg | acggcgtgta | catgaacgcc | accgtctggt | tcaacggcgt | caagctcggc | 480 |
| acccatccgt | acggctactc | gccgttctcc | ttcgacctga | ccggcaacgc | caagttcggt | 540 |
| ggggagaaca | ccatcgtcgt | caaggtcgag | aacaggctgc | cgtccagccg | ctggtactcc | 600 |
| ggctccggca | tctaccgcga | cgtcaccctc | accgtcaccg | acggcgtgca | cgtcggcaat | 660 |
| aacggcgtgg | ccatcaagac | cccgagcctc | gccacccaaa | acggcggcga | cgtgacgatg | 720 |
| aacctcacca | ccaaggtcgc | caacgacacc | gaggccgcgg | cgaacatcac | cctcaagcag | 780 |
| accgtgttcc | ccaagggagg | caagaccgac | gccgccatcg | gcaccgtcac | caccgcatcc | 840 |
| aagtccatcg | cggccggtgc | cagcgcggac | gtgacctcca | cgatcaccgc | cgcttcgccc | 900 |
| aagctgtgga | gcatcaagaa | cccgaacctg | tacaccgtgc | gcaccgaagt | gctcaacggc | 960 |
| ggcaaggtgc | tcgacactta | cgacaccgaa | tatggcttcc | gctggaccgg | cttcgatgcg | 1020 |
| accagcggtt | tctcgctcaa | cggcgagaaa | gtcaagctca | agggcgtctc | aatgcatcat | 1080 |
| gaccagggat | cgctcggcgc | ggtcgccaac | cgccgcgcca | tcgagcgcca | ggtcgagatt | 1140 |
| ctccagaaga | tgggcgtcaa | ctcgatccgc | accacgcaca | accccgcagc | caaggcgctg | 1200 |
| attgacgtct | gcaacgagaa | gggcgtcctc | gtggtcgaag | aggtcttcga | catgtggaac | 1260 |
| cggtcgaaga | acggcaacac | cgaggattac | ggcaagtggt | tcggccaggc | catcgccggt | 1320 |
| gacaacgccg | tcctgggtgg | cgacaaggac | gagacctggg | ccaagttcga | cctgaccagc | 1380 |
| accatcaacc | gtgacaggaa | cgccccgtcc | gtcatcatgt | ggtcgctcgg | caacgagatg | 1440 |
| atggaaggca | tcagcggcag | cgtctcgggc | ttcccggcta | cctccgccaa | gctggtcgca | 1500 |
| tggacgaagg | ccgcggacag | cacccgcccg | atgacctacg | cgacaacaa | gatcaaggcc | 1560 |
| aactggaacg | agtcgaacac | catgggcgac | aacctgaccg | ccaacggcgg | cgtggtcggc | 1620 |
| accaactact | ccgacggcgc | gaactacgac | aagatccgca | cgacccaccc | ctcatgggcc | 1680 |
| atctatggtt | ccgagacggc | gtccgccatc | aacagccgag | gcatctacaa | ccgcaccacc | 1740 |
| ggcggcgccc | agtcaagcga | caagcagctg | accagctatg | acaattccgc | agtcggctgg | 1800 |
| ggcgccgtcg | ccagctccgc | ctggtacgac | gtggtccagc | gcgatttcgt | cgccggcaca | 1860 |
| tacgtgtgga | ccggcttcga | ctacctcggc | gaacccaccc | cgtggaacgg | caccggctcc | 1920 |
| ggcgccgtgg | gctccttggc | cgtcgccgaa | gaactcgtac | ttcggcatcg | tcgacaccgc | 1980 |
| aggcttcccg | aagacaccta | ttacttctat | cagagccagt | ggaacgacga | cgtgcacacg | 2040 |
| ctgcacatcc | tccccgcatg | gaacgagaac | gtcgtcgcca | agggctccgg | caacaacgtg | 2100 |
| ccggtcgtcg | tctacaccga | cgcggccaag | gtcaagctgt | acttcacacc | gaagggcagt | 2160 |
| accgaaaagc | gactgatcgg | agagaagtcc | ttcaccaaga | agaccaccgc | ggccggatac | 2220 |
| acctatcagg | tctacgaggg | ctccgacaag | gactccaccg | cccacaagaa | catgtacctg | 2280 |
| acctggaacg | tgccgtgggc | cgagggcacc | atctccgccg | aagcatacga | cgagaacaac | 2340 |
| aggctgatcc | ccgagggtc | caccgagggc | aacgcgtcgg | tgaccaccac | cggcaaggcc | 2400 |
| gcgaagctta | agccgatgc | cgaccgcaag | acgatcaccg | cggacggcaa | ggacctgtcg | 2460 |
| tacatcgagg | tcgacgtgac | cgacgccaac | ggccatatcg | tccccgatgc | cgccaaccgc | 2520 |
| gtcaccttcg | acgtcaaggg | cgccggcaaa | ctggtcggcg | tcgacaacgg | cagctcgccg | 2580 |
| gatcacgact | cctatcaggc | cgacaaccgc | aaggcgttca | gcggcaaggt | gctcgccatc | 2640 |
| gtccagtcca | ccaaggaggc | gggcgagatc | accgtcaccg | ccaaggccga | cggtctgcaa | 2700 |
| tcatccacag | tgaagatcgc | caccaccgcc | gtccccggca | ccagcaccga | aagacggtc | 2760 |

```
cgcagcttct actactcgcg caactactac gtcaagaccg gcaacaagcc gattctgccg    2820
agtgatgtcg aggtgcgcta ctccgacggc acgtcggacc gtcagaacgt cacatgggac    2880
gcagtcagcg acgaccagat cgccaaggcc ggttcgttca gcgtggccgg cacggtcgcc    2940
gggcagaaga tctccgtgcg cgtgacgatg atcgacgaga tcggtgcgct gctcaactat    3000
tcggccagca caccggtcgg cacgcccgcc gtgctgcctg gctcgcgtcc ggccgtgctg    3060
cccgacggca ccgtgaccag cgcgaacttc gccgtccact ggaccaagcc cgccgacacc    3120
gtgtacaaca cggccggcac cgtcaaggtc cccggcaccg ccaccgtctt cggcaaggag    3180
ttcaaggtca ccgcgacgat cgcgtgcag cggtcgcagg tcaccatcgg cagcagcgtc    3240
tccggcaatg cgctgcgcct gactcagaac atccccgccg acaagcagtc cgacacgctg    3300
gacgccatca aggacggctc cacgaccgtc gacgccaata ccggcggcgg cgcgaacccg    3360
tcagcatgga ccaactgggc gtactcgaag gccggccaca acaccgccga gatcaccttc    3420
gagtacgcga ccgagcagca gctcggccag attgtcatgt acttcttccg cgacagcaac    3480
gcggtgaggt tccccgacgc cggcaagacg aagatccaga tctccgcgga cggcaagaac    3540
tggacggatc tcgctgccac ggagaccatc gcggcccagg agtcgtccga ccgagtcaag    3600
ccgtacacct atgacttcgc tccggtggga gccacgttcg tcaaggtcac ggtcaccaac    3660
gccgacacca caaccccccag cggcgtggtc tgcgccggcc tgaccgagat cgagctgaag    3720
accgcgacca gcaagttcgt cacgaacacg tccgccgcgc tctcgtcgct gacagtgaac    3780
ggcacgaagg tctccgactc cgtgctcgcc gccggctcct acaacacgcc cgcgatcatc    3840
gcggacgtca agccgagggg cgaaggcaac gccagcgtca ccgtgctgcc cgcgcacgac    3900
aacgtgatcc gcgtgatcac cgagtccgag gaccacgtca cgcgcaagac cttcaccatc    3960
aacctgggca cggagcagga attccccgca gactccgatg aacgcgacta cccggccgcc    4020
gacatgacgg tcaccgtggg cagcgaacag acgtccggca ccgcgaccga aggcccgaag    4080
aaattcgcgg tcgacggcaa caccagcacg tactggcatt ccaactggac gcccaccacc    4140
gtgaacgacc tgtggatcgc cttcgagctc cagaaaccca ccaagctcga cgcgctgcgc    4200
tacctgccgc gccccgcggg cagcaagaac ggctccgtca ccgaatacaa ggttcaggtc    4260
agcgatgacg gcaccaactg gaccgacgcg ggctccggca catggaccac cgattacggc    4320
tggaagctcg ccgagttcaa tcagccggtg accaccaagc acgtgcggct caaggccgtc    4380
cacacctatg cggattccgg caacgacaag ttcatgtccg cctccgaaat ccgcctgcgc    4440
aaggccgtcg acaccaccga catcagcggc gcgaccgtga ccgtgccgc caagctgacc    4500 gtcgaccggg tggacgccga ccatcccgcc accttcgcca cgaaggacgt gacggtgacg    4560
ttgggcgacg ccacgctgcg ctacggcgtg gactacctgc tcgactacgc gggcaacacc    4620
gccgtcggca aggccacggt gaccgtgcgc ggcatcgaca agtactccgg caccgtcgcc    4680
aagacgttca ccatcgaact gaagaacgcc ccggcgccgg aaccgacgct gacctcggtg    4740
agcgtcaaga ccaagccttc caagctgacc tatgtggtcg gcgacgcgtt cgacccggca    4800
ggactggtgc                                                          4810
```

<210> SEQ ID NO 4
<211> LENGTH: 3979
<212> TYPE: DNA
<213> ORGANISM: Bifidobacterium bifidum

<400> SEQUENCE: 4

```
atggcagttc gcagacttgg tggccgcatc gtggctttcg ccgccacagt ggccttgtca     60
```

-continued

```
ataccgttag ggttgttaac aaattcagcg tgggcggtcg aggacgccac ccgatccgac     120
tccaccacgc agatgagctc cacgccggag gtggtctact ccagcgccgt ggattccaag     180
cagaatcgca cctcggattt cgacgccaac tggaagttca tgctgtccga ttccgtgcag     240
gcgcaggatc cggcgttcga cgattcggcc tggcagcagg tcgacctgcc gcatgactac     300
agcatcacgc agaagtattc gcagagcaac gaggccgaaa gcgcatacct tcccggcggc     360
accggctggt accgcaagtc cttcaccatc gaccgggacc tcgccggcaa gcgcatcgcc     420
atcaacttcg acgcgtgta catgaacgcc accgtctggt tcaacggcgt caagctcggc     480
acccatccgt acggctactc gccgttctcc ttcgacctga ccggcaacgc caagttcggt     540
ggggagaaca ccatcgtcgt caaggtcgag aacaggctgc cgtccagccg ctggtactcc     600
ggctccggca tctaccgcga cgtcaccctc accgtcaccg acggcgtgca cgtcggcaat     660
aacggcgtgg ccatcaagac cccgagcctc gccacccaaa acgcggcga cgtgacgatg     720 aacctcacca ccaaggtcgc caacgacacc gaggccgcgg cgaacatcac cctcaagcag     780
accgtgttcc ccaagggagg caagaccgac gccgccatcg gcaccgtcac caccgcatcc     840
aagtccatcg cggccggtgc cagcgcggac gtgacctcca cgatcaccgc cgcttcgccc     900
aagctgtgga gcatcaagaa cccgaacctg tacaccgtgc gcaccgaagt gctcaacggc     960
ggcaaggtgc tcgacactta cgacaccgaa tatggcttcc gctggaccgg cttcgatgcg    1020
accagcggtt tctcgctcaa cggcgagaaa gtcaagctca agggcgtctc aatgcatcat    1080
gaccagggat cgctcggcgc ggtcgccaac cgccgcgcca tcgagcgcca ggtcgagatt    1140
ctccagaaga tgggcgtcaa ctcgatccgc accacgcaca ccccgcagc caaggcgctg    1200 attgacgtct gcaacgagaa gggcgtcctc gtggtcgaag aggtcttcga catgtggaac    1260
cggtcgaaga acggcaacac cgaggattac ggcaagtggt tcggccaggc catcgccggt    1320
gacaacgccg tcctgggtgg cgacaaggac gagacctggg ccaagttcga cctgaccagc    1380
accatcaacc gtgacaggaa cgccccgtcc gtcatcatgt ggtcgctcgg caacgagatg    1440
atggaaggca tcagcggcag cgtctcgggc ttcccggcta cctccgccaa gctggtcgca    1500
tggacgaagg ccgcggacag caccgcccg atgacctacg cgacaacaa gatcaaggcc    1560 aactggaacg agtcgaacac catgggcgac aacctgaccg ccaacggcgg cgtggtcggc    1620
accaactact ccgacggcgc gaactacgac aagatccgca cgaccacccc ctcatgggcc    1680
atctatggtt ccgagacggc gtccgccatc aacagccgag gcatctacaa ccgcaccacc    1740
ggcggcgccc agtcaagcga caagcagctg accagctatg acaattccgc agtcggctgg    1800
ggcgccgtcg ccagctccgc ctggtacgac gtggtccagc gcgatttcgt cgccggcaca    1860
tacgtgtgga ccggcttcga ctacctcggc gaacccaccc cgtggaacgg caccggctcc    1920
ggcgccgtgg gctccttggc cgtcgccgaa gaactcgtac ttcggcatcg tcgacaccgc    1980
aggcttcccg aagacaccta ttacttctat cagagccagt ggaacgacga cgtgcacacg    2040
ctgcacatcc tccccgcatg gaacgagaac gtcgtcgcca gggctccgg caacaacgtg    2100 ccggtcgtcg tctacaccga cgcggccaag gtcaagctgt acttcacacc gaagggcagt    2160
accgaaaagc gactgatcgg agagaagtcc ttcaccaaga agaccaccgc ggccggatac    2220
acctatcagg tctacgaggg ctccgacaag gactccaccg cccacaagaa catgtacctg    2280
acctggaacg tgccgtgggc cgagggcacc atctccgccg aagcatacga cgagaacaac    2340
aggctgatcc ccgagggggtc caccgagggc aacgcgtcgg tgaccaccac cggcaaggcc    2400
```

-continued

```
gcgaagctta aagccgatgc cgaccgcaag acgatcaccg cggacggcaa ggacctgtcg    2460
tacatcgagg tcgacgtgac cgacgccaac ggccatatcg tccccgatgc cgccaaccgc    2520
gtcaccttcg acgtcaaggg cgccggcaaa ctggtcggcg tcgacaacgg cagctcgccg    2580
gatcacgact cctatcaggc cgacaaccgc aaggcgttca gcggcaaggt gctcgccatc    2640
gtccagtcca ccaaggaggc gggcgagatc accgtcaccg ccaaggccga cggtctgcaa    2700
tcatccacag tgaagatcgc caccaccgcc gtccccggca ccagcaccga agacggtc      2760 cgcagcttct actactcgcg caactactac gtcaagaccg gcaacaagcc gattctgccg    2820
agtgatgtcg aggtgcgcta ctccgacggc acgtcggacc gtcagaacgt cacatgggac    2880
gcagtcagcg acgaccagat cgccaaggcc ggttcgttca gcgtggccgg cacggtcgcc    2940
gggcagaaga tctccgtgcg cgtgacgatg atcgacgaga tcggtgcgct gctcaactat    3000
tcggccagca caccggtcgg cacgcccgcc gtgctgcctg ctcgcgtcc ggccgtgctg      3060 cccgacggca ccgtgaccag cgcgaacttc gccgtccact ggaccaagcc cgccgacacc    3120
gtgtacaaca cggccggcac cgtcaaggtc cccggcaccg ccaccgtctt cggcaaggag    3180
ttcaaggtca ccgcgacgat tcgcgtgcag cggtcgcagg tcaccatcgg cagcagcgtc    3240
tccggcaatg cgctgcgcct gactcagaac atccccgccg acaagcagtc cgacacgctg    3300
gacgccatca aggacggctc cacgaccgtc gacgccaata ccggcggcgg cgcgaacccg    3360
tcagcatgga ccaactgggc gtactcgaag gccggccaca acaccgccga gatcaccttc    3420
gagtacgcga ccgagcagca gctcggccag attgtcatgt acttcttccg cgacagcaac    3480
gcggtgaggt tccccgacgc cggcaagacg aagatccaga tctccgcgga cggcaagaac    3540
tggacggatc tcgctgccac ggagaccatc gcggcccagg agtcgtccga ccgagtcaag    3600
ccgtacacct atgacttcgc tccggtggga gccacgttcg tcaaggtcac ggtcaccaac    3660
gccgacacca caaccccag cggcgtggtc tgcgccggcc tgaccgagat cgagctgaag     3720
accgcgacca gcaagttcgt cacgaacacg tccgccgcgc tctcgtcgct gacagtgaac    3780
ggcacgaagg tctccgactc cgtgctcgcc gccggctcct acaacacgcc cgcgatcatc    3840
gcggacgtca agccgagggc gaaggcaac gccagcgtca ccgtgctgcc cgcgcacgac     3900
aacgtgatcc gcgtgatcac cgagtccgag gaccacgtca cgcgcaagac cttcaccatc    3960
aacctgggca cggagcagg                                                 3979
```

<210> SEQ ID NO 5
<211> LENGTH: 3518
<212> TYPE: DNA
<213> ORGANISM: Bifidobacterium bifidum

<400> SEQUENCE: 5

```
atggcagttc gcagacttgg tggccgcatc gtggctttcg ccgccacagt ggccttgtca     60
ataccgttag ggttgttaac aaattcagcg tgggcggtcg aggacgccac ccgatccgac    120
tccaccacgc agatgagctc cacgccgag gtggtctact ccagcgccgt ggattccaag     180
cagaatcgca cctcggattt cgacgccaac tggaagttca tgctgtccga ttccgtgcag    240
gcgcaggatc cggcgttcga cgattcggcc tggcagcagg tcgacctgcc gcatgactac    300
agcatcacgc agaagtattc gcagagcaac gaggccgaaa gcgcatacct tcccggcggc    360
accggctggt accgcaagtc cttcaccatc gaccgggacc tcgccggcaa cgcatcgcc    420 atcaacttcg acgcgtgta catgaacgcc accgtctggt caacggcgt caagctcggc    480 acccatccgt acggctactc gccgttctcc ttcgacctga ccggcaacgc caagttcggt    540
```

-continued

```
ggggagaaca ccatcgtcgt caaggtcgag aacaggctgc cgtccagccg ctggtactcc     600
ggctccggca tctaccgcga cgtcaccctc accgtcaccg acggcgtgca cgtcggcaat     660
aacggcgtgg ccatcaagac cccgagcctc gccacccaaa acggcggcga cgtgacgatg     720
aacctcacca ccaaggtcgc caacgacacc gaggccgcgg cgaacatcac cctcaagcag     780
accgtgttcc caagggagg caagaccgac gccgccatcg gcaccgtcac caccgcatcc     840
aagtccatcg cggccggtgc cagcgcggac gtgacctcca cgatcaccgc cgcttcgccc     900
aagctgtgga gcatcaagaa cccgaacctg tacaccgtgc gcaccgaagt gctcaacggc     960
ggcaaggtgc tcgacactta cgacaccgaa tatggcttcc gctggaccgg cttcgatgcg    1020
accagcggtt tctcgctcaa cggcgagaaa gtcaagctca agggcgtctc aatgcatcat    1080
gaccagggat cgctcggcgc ggtcgccaac cgccgcgcca tcgagcgcca ggtcgagatt    1140
ctccagaaga tgggcgtcaa ctcgatccgc accacgcaca accccgcagc caaggcgctg    1200
attgacgtct gcaacgagaa gggcgtcctc gtggtcgaag aggtcttcga catgtggaac    1260
cggtcgaaga acggcaacac cgaggattac ggcaagtggt tcggccaggc catcgccggt    1320
gacaacgccg tcctgggtgg cgacaaggac gagacctggg ccaagttcga cctgaccagc    1380
accatcaacc gtgacaggaa cgccccgtcc gtcatcatgt ggtcgctcgg caacgagatg    1440
atggaaggca tcagcggcag cgtctcgggc ttccggctg cctccgccaa gctggtcgca    1500
tggacgaagg ccgcggacag cacccgcccg atgacctacg cgacaacaa gatcaaggcc    1560 aactggaacg agtcgaacac catgggcgac aacctgaccg ccaacggcgg cgtggtcggc    1620
accaactact ccgacggcgc gaactacgac aagatccgca cgaccaccc ctcatgggcc    1680 atctatggtt ccgagacggc gtccgccatc aacagccgag gcatctacaa ccgcaccacc    1740
ggcggcgccc agtcaagcga caagcagctg accagctatg acaattccgc agtcggctgg    1800
ggcgccgtcg ccagctccgc ctggtacgac gtggtccagc gcgatttcgt cgccggcaca    1860
tacgtgtgga ccggcttcga ctacctcggc gaacccaccc cgtggaacgg caccggctcc    1920
ggcgccgtgg gctccttggc cgtcgccgaa gaactcgtac ttcggcatcg tcgacaccgc    1980
aggcttcccg aagacaccta ttacttctat cagagccagt ggaacgacga cgtgcacacg    2040
ctgcacatcc tccccgcatg gaacgagaac gtcgtcgcca gggctccgg caacaacgtg    2100 ccggtcgtcg tctacaccga cgcggccaag gtcaagctgt acttcacacc gaagggcagt    2160
accgaaaagc gactgatcgg agagaagtcc ttcaccaaga agaccaccgc ggccggatac    2220
acctatcagg tctacgaggg ctccgacaag gactccaccg cccacaagaa catgtacctg    2280
acctggaacg tgccgtgggc cgagggcacc atctccgccc aagcatacga cgagaacaac    2340
aggctgatcc ccgagggtc caccgagggc aacgcgtcgg tgaccaccac cggcaaggcc    2400
gcgaagctta aagccgatgc cgaccgcaag acgatcaccg cggacggcaa ggacctgtcg    2460
tacatcgagg tcgacgtgac cgacgccaac ggccatatcg tccccgatgc cgccaaccgc    2520
gtcaccttcg acgtcaaggg cgccggcaaa ctggtcggcg tcgacaacgg cagctcgccg    2580
gatcacgact cctatcaggc cgacaaccgc aaggcgttca gcggcaaggt gctcgccatc    2640
gtccagtcca ccaaggaggc gggcgagatc accgtcaccg ccaaggccga cggtctgcaa    2700
tcatccacag tgaagatcgc caccaccgcc gtccccggca ccagcaccga aagacggtc    2760 cgcagcttct actactcgcg caactactac gtcaagaccg caacaagcc gattctgccg    2820 agtgatgtcg aggtgcgcta ctccgacggc acgtcggacc gtcagaacgt cacatgggac    2880
```

-continued

| | |
|---|---|
| gcagtcagcg acgaccagat cgccaaggcc ggttcgttca gcgtggccgg cacggtcgcc | 2940 |
| gggcagaaga tctccgtgcg cgtgacgatg atcgacgaga tcggtgcgct gctcaactat | 3000 |
| tcggccagca caccggtcgg cacgcccgcc gtgctgcctg ctcgcgtcc ggccgtgctg | 3060 |
| cccgacggca ccgtgaccag cgcgaacttc gccgtccact ggaccaagcc cgccgacacc | 3120 |
| gtgtacaaca cggccggcac cgtcaaggtc cccggcaccg ccaccgtctt cggcaaggag | 3180 |
| ttcaaggtca ccgcgacgat tcgcgtgcag cggtcgcagg tcaccatcgg cagcagcgtc | 3240 |
| tccggcaatg cgctgcgcct gactcagaac atccccgccg acaagcagtc cgacacgctg | 3300 |
| gacgccatca aggacggctc cacgaccgtc gacgccaata ccggcggcgg cgcgaacccg | 3360 |
| tcagcatgga ccaactgggc gtactcgaag gccggccaca acaccgccga gatcaccttc | 3420 |
| gagtacgcga ccgagcagca gctcggccag attgtcatgt acttcttccg cgacagcaac | 3480 |
| gcggtgaggt tccccgacgc cggcaagacg aagatcca | 3518 |

<210> SEQ ID NO 6
<211> LENGTH: 2948
<212> TYPE: DNA
<213> ORGANISM: Bifidobacterium bifidum

<400> SEQUENCE: 6

| | |
|---|---|
| atggcagttc gcagacttgg tggccgcatc gtggctttcg ccgccacagt ggccttgtca | 60 |
| ataccgttag ggttgttaac aaattcagcg tgggcggtcg aggacgccac ccgatccgac | 120 |
| tccaccacgc agatgagctc cacgccgag gtggtctact ccagcgccgt ggattccaag | 180 |
| cagaatcgca cctcggattt cgacgccaac tggaagttca tgctgtccga ttccgtgcag | 240 |
| gcgcaggatc cggcgttcga cgattcggcc tggcagcagg tcgacctgcc gcatgactac | 300 |
| agcatcacgc agaagtattc gcagagcaac gaggccgaaa gcgcatacct tccggcggc | 360 |
| accggctggt accgcaagtc cttcaccatc gaccgggacc tcgccggcaa gcgcatcgcc | 420 |
| atcaacttcg acggcgtgta catgaacgcc accgtctggt tcaacggcgt caagctcggc | 480 |
| acccatccgt acggctactc gccgttctcc ttcgacctga ccggcaacgc caagttcggt | 540 |
| ggggagaaca ccatcgtcgt caaggtcgag aacaggctgc cgtccagccg ctggtactcc | 600 |
| ggctccggca tctaccgcga cgtcaccctc ccgtcaccg acggcgtgca cgtcggcaat | 660 |
| aacggcgtgg ccatcaagac cccgagcctc gccacccaaa acggcggcga cgtgacgatg | 720 |
| aacctcacca ccaaggtcgc caacgacacc gaggccgcgg cgaacatcac cctcaagcag | 780 |
| accgtgttcc ccaagggagg caagaccgac gccgccatcg gcaccgtcac caccgcatcc | 840 |
| aagtccatcg cggccggtgc cagcgcggac gtgacctcca cgatcaccgc cgcttcgccc | 900 |
| aagctgtgga gcatcaagaa cccgaacctg tacaccgtgc gcaccgaagt gctcaacggc | 960 |
| ggcaaggtgc tcgacactta cgacaccgaa tatggcttcc gctggaccgg cttcgatgcg | 1020 |
| accagcggtt tctcgctcaa cggcgagaaa gtcaagctca gggcgtctc aatgcatcat | 1080 |
| gaccagggat cgctcggcgc ggtcgccaac cgccgcgcca tcgagcgcca ggtcgagatt | 1140 |
| ctccagaaga tgggcgtcaa ctcgatccgc accacgcaca ccccgcagc caaggcgctg | 1200 |
| attgacgtct gcaacgagaa gggcgtcctc gtggtcgaag aggtcttcga catgtggaac | 1260 |
| cggtcgaaga acggcaacac cgaggattac ggcaagtggt cggccaggc catcgccggt | 1320 |
| gacaacgccg tcctgggtgg cgacaaggac gagacctggg ccaagttcga cctgaccagc | 1380 |
| accatcaacc gtgacaggaa cgccccgtcc gtcatcatgt ggtcgtcgg caacgagatg | 1440 |
| atggaaggca tcagcggcag cgtctcgggc ttcccggcta cctccgccaa gctggtcgca | 1500 |

```
tggacgaagg ccgcggacag cacccgcccg atgacctacg gcgacaacaa gatcaaggcc    1560
aactggaacg agtcgaacac catgggcgac aacctgaccg ccaacggcgg cgtggtcggc    1620
accaactact ccgacggcgc gaactacgac aagatccgca cgacccaccc ctcatgggcc    1680
atctatggtt ccgagacggc gtccgccatc aacagccgag gcatctacaa ccgcaccacc    1740
ggcggcgccc agtcaagcga caagcagctg accagctatg acaattccgc agtcggctgg    1800
ggcgccgtcg ccagctccgc ctggtacgac gtggtccagc gcgatttcgt cgccggcaca    1860
tacgtgtgga ccggcttcga ctacctcggc gaacccaccc cgtggaacgg caccggctcc    1920
ggcgccgtgg gctccttggc cgtcgccgaa gaactcgtac ttcggcatcg tcgacaccgc    1980
aggcttcccg aagacaccta ttacttctat cagagccagt ggaacgacga cgtgcacacg    2040
ctgcacatcc tccccgcatg aacgagaac gtcgtcgcca agggctccgg caacaacgtg    2100
ccggtcgtcg tctacaccga cgcggccaag gtcaagctgt acttcacacc gaagggcagt    2160
accgaaaagc gactgatcgg agagaagtcc ttcaccaaga agaccaccgc ggccggatac    2220
acctatcagg tctacgaggg ctccgacaag gactccaccg cccacaagaa catgtacctg    2280
acctggaacg tgccgtgggc cgagggcacc atctccgccg aagcatacga cgagaacaac    2340
aggctgatcc ccgaggggtc caccgagggc aacgcgtcgg tgaccaccac cggcaaggcc    2400
gcgaagctta agccgatgc cgaccgcaag acgatcaccg cggacggcaa ggacctgtcg    2460
tacatcgagg tcgacgtgac cgacgccaac ggccatatcg tccccgatgc cgccaaccgc    2520
gtcaccttcg acgtcaaggg cgccggcaaa ctggtcggcg tcgacaacgg cagctcgccg    2580
gatcacgact cctatcaggc cgacaaccgc aaggcgttca gcggcaaggt gctcgccatc    2640
gtccagtcca ccaaggaggc gggcgagatc accgtcaccg ccaaggccga cggtctgcaa    2700
tcatccacag tgaagatcgc caccaccgcc gtccccggca ccagcaccga aagacggtc     2760 cgcagcttct actactcgcg caactactac gtcaagaccg gcaacaagcc gattctgccg    2820
agtgatgtcg aggtgcgcta ctccgacggc acgtcggacc gtcagaacgt cacatgggac    2880
gcagtcagcg acgaccagat cgccaaggcc ggttcgttca gcgtggccgg cacggtcgcc    2940
gggcagaa                                                            2948

<210> SEQ ID NO 7
<211> LENGTH: 5163
<212> TYPE: DNA
<213> ORGANISM: Bifidobacterium bifidum

<400> SEQUENCE: 7
gtcgaggacg ccacccgatc cgactccacc acgcagatga gctccacgcc ggaggtggtc      60
tactccagcg ccgtggattc caagcagaat cgcacctcgg atttcgacgc caactggaag     120
ttcatgctgt ccgattccgt gcaggcgcag gatccggcgt tcgacgattc ggcctggcag     180
caggtcgacc tgccgcatga ctacagcatc acgcagaagt attcgcagag caacgaggcc     240
gaaagcgcat accttcccgg cggcaccggc tggtaccgca agtccttcac catcgaccgg     300
gacctcgccg gcaagcgcat cgccatcaac ttcgacggcg tgtacatgaa cgccaccgtc     360
tggttcaacg gcgtcaagct cggcacccat ccgtacggct actcgccgtt ctccttcgac     420
ctgaccggca cgccaagtt cggtggggag aacaccatcg tcgtcaaggt cgagaacagg     480
ctgccgtcca gccgctggta ctccggctcc ggcatctacc gcgacgtcac cctcaccgtc     540
accgacggcg tgcacgtcgg caataacggc gtggccatca agacccgag cctcgccacc     600
```

-continued

```
caaaacggcg gcgacgtgac gatgaacctc accaccaagg tcgccaacga caccgaggcc    660
gcggcgaaca tcaccctcaa gcagaccgtg ttccccaagg gaggcaagac cgacgccgcc    720
atcggcaccg tcaccaccgc atccaagtcc atcgcggccg gtgccagcgc ggacgtgacc    780
tccacgatca ccgccgcttc gcccaagctg tggagcatca agaacccgaa cctgtacacc    840
gtgcgcaccg aagtgctcaa cggcggcaag gtgctcgaca cttacgacac cgaatatggc    900
ttccgctgga ccggcttcga tgcgaccagc ggtttctcgc tcaacggcga gaaagtcaag    960
ctcaagggcg tctcaatgca tcatgaccag ggatcgctcg gcgcggtcgc caaccgccgc   1020
gccatcgagc gccaggtcga gattctccag aagatgggcg tcaactcgat ccgcaccacg   1080
cacaaccccg cagccaaggc gctgattgac gtctgcaacg agaagggcgt cctcgtggtc   1140
gaagaggtct tcgacatgtg gaaccggtcg aagaacggca acaccgagga ttacggcaag   1200
tggttcggcc aggccatcgc cggtgacaac gccgtcctgg gtggcgacaa ggacgagacc   1260
tgggccaagt tcgacctgac cagcaccatc aaccgtgaca ggaacgcccc gtccgtcatc   1320
atgtggtcgc tcggcaacga gatgatgaa ggcatcagcg gcagcgtctc gggcttcccg   1380
gctacctccg ccaagctggt cgcatggacg aaggccgcgg acagcacccg cccgatgacc   1440
tacggcgaca acaagatcaa ggccaactgg aacgagtcga acaccatggg cgacaacctg   1500
accgccaacg gcggcgtggt cggcaccaac tactccgacg gcgcgaacta cgacaagatc   1560
cgcacgaccc acccctcatg ggccatctat ggttccgaga cggcgtccgc catcaacagc   1620
cgaggcatct acaaccgcac caccggcggc gcccagtcaa gcgacaagca gctgaccagc   1680
tatgacaatt ccgcagtcgg ctggggcgcc gtcgccagct ccgcctggta cgacgtggtc   1740
cagcgcgatt tcgtcgccgg cacatacgtg tggaccggct tcgactacct cggcgaaccc   1800
accccgtgga acggcaccgg ctccggcgcc gtgggctcct tggccgtcgc cgaagaactc   1860
gtacttcggc atcgtcgaca ccgcaggctt cccgaagaca cctattactt ctatcagagc   1920
cagtggaacg acgacgtgca cacgctgcac atcctccccg catggaacga aacgtcgtc    1980
gccagggct ccgcaacaa cgtgccggtc gtcgtctaca ccgacgcggc caaggtcaag    2040
ctgtacttca caccgaaggg cagtaccgaa aagcgactga tcggagagaa gtccttcacc   2100
aagaagacca ccgcggccgg atacacctat caggtctacg agggctccga caaggactcc   2160
accgcccaca gaacatgta cctgacctgg aacgtgccgt gggccgaggg caccatctcc   2220
gccgaagcat acgacgagaa caacaggctg atccccgagg gtccaccgga gggcaacgcg   2280
tcggtgacca ccaccggcaa ggccgcgaag cttaaagccg atgccgaccg caagacgatc   2340
accgcggacg gcaaggacct gtcgtacatc gaggtcgacg tgaccgacgc caacggccat   2400
atcgtccccg atgccgccaa ccgcgtcacc ttcgacgtca agggcgccgg caaactggtc   2460
ggcgtcgaca acgcagctc gccggatcac gactcctatc aggccgacaa ccgcaaggcg   2520
ttcagcggca aggtgctcgc catcgtccag tccaccaagg aggcgggcga gatcaccgtc   2580
accgccaagg ccgacggtct gcaatcatcc acagtgaaga tcgccaccac cgccgtcccc   2640
ggcaccagca ccgagaagac ggtccgcagc ttctactact cgcgcaacta ctacgtcaag   2700
accggcaaca agccgattct gccgagtgat gtcgaggtgc gctactccga cggcacgtcg   2760
gaccgtcaga acgtcacatg ggacgcagtc agcgacgacc agatcgccaa ggccggttcg   2820
ttcagcgtgg ccggcacggt cgccgggcag aagatctccg tgcgcgtgac gatgatcgac   2880
gagatcggtg cgctgctcaa ctattcggcc agcacaccgg tcggcacgcc cgccgtgctg   2940
cctggctcgc gtccggccgt gctgcccgac ggcaccgtga ccagcgcgaa cttcgccgtc   3000
```

```
cactggacca agcccgccga caccgtgtac aacacggccg gcaccgtcaa ggtccccggc      3060
accgccaccg tcttcggcaa ggagttcaag gtcaccgcga cgattcgcgt gcagcggtcg      3120
caggtcacca tcggcagcag cgtctccggc aatgcgctgc gcctgactca gaacatcccc      3180
gccgacaagc agtccgacac gctggacgcc atcaaggacg gctccacgac cgtcgacgcc      3240
aataccggcg gcggcgcgaa cccgtcagca tggaccaact gggcgtactc gaaggccggc      3300
cacaacaccg ccgagatcac cttcgagtac gcgaccgagc agcagctcgg ccagattgtc      3360
atgtacttct ccgcgacag caacgcggtg aggttccccg acgccggcaa gacgaagatc      3420
cagatctccg cggacggcaa gaactggacg gatctcgctg ccacggagac catcgcggcc      3480
caggagtcgt ccgaccgagt caagccgtac acctatgact tcgctccggt gggagccacg      3540
ttcgtcaagg tcacggtcac aacgccgac accacaaccc ccagcggcgt ggtctgcgcc      3600
ggcctgaccg agatcgagct gaagaccgcg accagcaagt tcgtcacgaa cacgtccgcc      3660
gcgctctcgt cgctgacagt gaacggcacg aaggtctccg actccgtgct cgccgccggc      3720
tcctacaaca cgcccgcgat catcgcggac gtcaaagccg agggcgaagg caacgccagc      3780
gtcaccgtgc tgcccgcgca cgacaacgtg atccgcgtga tcaccgagtc cgaggaccac      3840
gtcacgcgca agaccttcac catcaacctg ggcacggagc aggaattccc cgcagactcc      3900
gatgaacgcg actaccggc cgccgacatg acggtcaccg tgggcagcga acagacgtcc      3960
ggcaccgcga ccgaaggccc gaagaaattc gcggtcgacg caacaccag cacgtactgg      4020
cattccaact ggacgcccac caccgtgaac gacctgtgga tcgccttcga gctccagaaa      4080
cccaccaagc tcgacgcgct cgcgctacctg ccgcgcccg cgggcagcaa gaacggctcc      4140
gtcaccgaat acaaggttca ggtcagcgat gacggcacca actggaccga cgcgggctcc      4200
ggcacatgga ccaccgatta cggctggaag ctcgccgagt tcaatcagcc ggtgaccacc      4260
aagcacgtgc ggctcaaggc cgtccacacc tatgcggatt ccggcaacga caagttcatg      4320
tccgcctccg aaatccgcct gcgcaaggcc gtcgacacca ccgacatcag cggcgcgacc      4380
gtgaccgtgc ccgccaagct gaccgtcgac cgggtggacg ccgaccatcc cgccaccttc      4440
gccacgaagg acgtgacggt gacgttgggc gacgccacgc tgcgctacgg cgtggactac      4500
ctgctcgact acgcgggcaa caccgccgtc ggcaaggcca cggtgaccgt gcgcggcatc      4560
gacaagtact ccggcaccgt cgccaagacg ttcaccatcg aactgaagaa cgccccggcg      4620
ccggaaccga cgctgacctc ggtgagcgtc aagaccaagc cttccaagct gacctatgtg      4680
gtcggcgacg cgttcgaccc ggcaggactg gtgctgcagc acgacagaca ggccgatcgc      4740
cccccacagc cacttgttgg agaacaggcc gacgaacgcg gactgacgtg cggaacgcga      4800
tgcgatcgcg ttgaacagct gcgcaaacac gagaatcgtg aagcccatcg tacgggcctc      4860
gatcatctgg aattcgtggg tgccgccgat ggagcggtcg gtgaacaggc caccttcaag      4920
gtgcatgtcc atgccgatca aggtgacggc cgccatgatg atgccgatga acgcgatatc      4980
gatccacatg tccctgtcga tcacgcggtc ggtgagcttg cgcgggctgc gtgccatcac      5040
gtcatcggtc tgcgggtcga cacccatcgc ctcaaggcat ccggcttcca gatccccgcc      5100
gacgacatgg ccgagatcga ccgcatcacc ggcttccacc gcttcgagcg ccacgtcggc      5160
tga                                                                   5163
```

<210> SEQ ID NO 8
<211> LENGTH: 3427
<212> TYPE: DNA

<213> ORGANISM: Bifidobacterium bifidum

<400> SEQUENCE: 8

| | | | | | |
|---|---|---|---|---|---|
| gtcgaggacg | ccacccgatc | cgactccacc | acgcagatga | gctccacgcc | ggaggtggtc | 60 |
| tactccagcg | ccgtggattc | caagcagaat | cgcacctcgg | atttcgacgc | caactggaag | 120 |
| ttcatgctgt | ccgattccgt | gcaggcgcag | gatccggcgt | tcgacgattc | ggcctggcag | 180 |
| caggtcgacc | tgccgcatga | ctacagcatc | acgcagaagt | attcgcagag | caacgaggcc | 240 |
| gaaagcgcat | accttcccgg | cggcaccggc | tggtaccgca | agtccttcac | catcgaccgg | 300 |
| gacctcgccg | gcaagcgcat | cgccatcaac | ttcgacggcg | tgtacatgaa | cgccaccgtc | 360 |
| tggttcaacg | gcgtcaagct | cggcacccat | ccgtacggct | actcgccgtt | ctccttcgac | 420 |
| ctgaccggca | acgccaagtt | cggtggggag | aacaccatcg | tcgtcaaggt | cgagaacagg | 480 |
| ctgccgtcca | gccgctggta | ctccggctcc | ggcatctacc | gcgacgtcac | cctcaccgtc | 540 |
| accgacggcg | tgcacgtcgg | caataacggc | gtggccatca | agaccccgag | cctcgccacc | 600 |
| caaaacggcg | cgacgtgac | gatgaacctc | accaccaagg | tcgccaacga | caccgaggcc | 660 |
| gcggcgaaca | tcaccctcaa | gcagaccgtg | ttccccaagg | gaggcaagac | cgacgccgcc | 720 |
| atcggcaccg | tcaccaccgc | atccaagtcc | atcgcggccg | tgccagcgc | ggacgtgacc | 780 |
| tccacgatca | ccgccgcttc | gcccaagctg | tggagcatca | agaacccgaa | cctgtacacc | 840 |
| gtgcgcaccg | aagtgctcaa | cggcggcaag | gtgctcgaca | cttacgacac | cgaatatggc | 900 |
| ttccgctgga | ccggcttcga | tgcgaccagc | ggtttctcgc | tcaacggcga | gaaagtcaag | 960 |
| ctcaagggcg | tctcaatgca | tcatgaccag | ggatcgctcg | gcgcggtcgc | caaccgccgc | 1020 |
| gccatcgagc | gccaggtcga | gattctccag | aagatgggcg | tcaactcgat | ccgcaccacg | 1080 |
| cacaaccccg | cagccaaggc | gctgattgac | gtctgcaacg | agaagggcgt | cctcgtggtc | 1140 |
| gaagaggtct | tcgacatgtg | gaaccggtcg | aagaacggca | acaccgagga | ttacggcaag | 1200 |
| tggttcggcc | aggccatcgc | cggtgacaac | gccgtcctgg | gtggcgacaa | ggacgagacc | 1260 |
| tgggccaagt | tcgacctgac | cagcaccatc | aaccgtgaca | ggaacgcccc | gtccgtcatc | 1320 |
| atgtggtcgc | tcggcaacga | gatgatggaa | ggcatcagcg | gcagcgtctc | gggcttcccg | 1380 |
| gctacctccg | ccaagctggt | cgcatggacg | aaggccgcgg | acagcacccg | cccgatgacc | 1440 |
| tacggcgaca | caagatcaa | ggccaactgg | aacgagtcga | acaccatggg | cgacaacctg | 1500 |
| accgccaacg | gcggcgtggt | cggcaccaac | tactccgacg | gcgcgaacta | cgacaagatc | 1560 |
| cgcacgaccc | acccctcatg | ggccatctat | ggttccgaga | cggcgtccgc | catcaacagc | 1620 |
| cgaggcatct | acaaccgcac | caccggcggc | gcccagtcaa | gcgacaagca | gctgaccagc | 1680 |
| tatgacaatt | ccgcagtcgg | ctggggcgcc | gtcgccagct | ccgcctggta | cgacgtggtc | 1740 |
| cagcgcgatt | tcgtcgccgg | cacatacgtg | tggaccggct | tcgactacct | cggcgaaccc | 1800 |
| accccgtgga | acggcaccgg | ctccggcgcc | gtgggctcct | tggccgtcgc | cgaagaactc | 1860 |
| gtacttcggc | atcgtcgaca | ccgcaggctt | cccgaagaca | cctattactt | ctatcagagc | 1920 |
| cagtggaacg | acgacgtgca | cacgctgcac | atcctccccg | catggaacga | gaacgtcgtc | 1980 |
| gccaagggct | ccggcaacaa | cgtgccggtc | gtcgtctaca | ccgacgcggc | caaggtcaag | 2040 |
| ctgtacttca | caccgaaggg | cagtaccgaa | aagcgactga | tcggagagaa | gtccttcacc | 2100 |
| aagaagacca | ccgcggccgg | atacacctat | caggtctacg | agggctccga | caaggactcc | 2160 |
| accgcccaca | agaacatgta | cctgacctgg | aacgtgccgt | gggccgaggg | caccatctcc | 2220 |
| gccgaagcat | acgacgagaa | caacaggctg | atccccgagg | ggtccaccga | gggcaacgcg | 2280 |

-continued

```
tcggtgacca ccaccggcaa ggccgcgaag cttaaagccg atgccgaccg caagacgatc    2340
accgcggacg gcaaggacct gtcgtacatc gaggtcgacg tgaccgacgc caacggccat    2400
atcgtccccg atgccgccaa ccgcgtcacc ttcgacgtca agggcgccgg caaactggtc    2460
ggcgtcgaca acggcagctc gccggatcac gactcctatc aggccgacaa ccgcaaggcg    2520
ttcagcggca aggtgctcgc catcgtccag tccaccaagg aggcgggcga gatcaccgtc    2580
accgccaagg ccgacggtct gcaatcatcc acagtgaaga tcgccaccac cgccgtcccc    2640
ggcaccagca ccgagaagac ggtccgcagc ttctactact cgcgcaacta ctacgtcaag    2700
accggcaaca agccgattct gccgagtgat gtcgaggtgc gctactccga cggcacgtcg    2760
gaccgtcaga acgtcacatg ggacgcagtc agcgacgacc agatcgccaa ggccggttcg    2820
ttcagcgtgg ccggcacggt cgccgggcag aagatctccg tgcgcgtgac gatgatcgac    2880
gagatcggtg cgctgctcaa ctattcggcc agcacaccgg tcggcacgcc cgccgtgctg    2940
cctggctcgc gtccggccgt gctgcccgac ggcaccgtga ccagcgcgaa cttcgccgtc    3000
cactggacca agcccgccga caccgtgtac aacacgcccg caccgtcaa ggtccccggc    3060 accgccaccg tcttcggcaa ggagttcaag gtcaccgcga cgattcgcgt gcagcggtcg    3120
caggtcacca tcggcagcag cgtctccggc aatgcgctgc gcctgactca gaacatcccc    3180
gccgacaagc agtccgacac gctggacgcc atcaaggacg gctccacgac cgtcgacgcc    3240
aataccggcg gcgcgcgcaa cccgtcagca tggaccaact gggcgtactc gaaggccggc    3300
cacaacaccg ccgagatcac cttcgagtac gcgaccgagc agcagctcgg ccagattgtc    3360
atgtacttct ccgcgacag caacgcggtg aggttccccg acgccggcaa gacgaagatc    3420
cagatct                                                              3427
```

<210> SEQ ID NO 9
<211> LENGTH: 42
<212> TYPE: PRT
<213> ORGANISM: Escherichia coli

<400> SEQUENCE: 9

Arg Phe Leu Ala Ala Ser Gln Ala Tyr Leu Asp Ala Leu Ala Lys Gln
1               5                   10                  15

Val Gln Pro Leu Leu Asn His Asn Gly Gly Pro Ile Ile Ala Val Gln
            20                  25                  30

Val Glu Asn Glu Tyr Gly Ser Tyr Ala Asp
        35                  40

<210> SEQ ID NO 10
<211> LENGTH: 44
<212> TYPE: PRT
<213> ORGANISM: Escherichia coli

<400> SEQUENCE: 10

His Tyr Cys Pro Asn His Pro Gln Leu Ile Thr His Ile Lys Arg Leu
1               5                   10                  15

Val Arg Ala Ile Ala Glu Arg Tyr Lys Asn His Pro Ala Leu Lys Met
            20                  25                  30

Trp His Val Asn Asn Glu Tyr Ala Cys His Val Ser
        35                  40

<210> SEQ ID NO 11
<211> LENGTH: 46
<212> TYPE: PRT

<213> ORGANISM: Escherichia coli

<400> SEQUENCE: 11

Thr Ile Ser Ser Ser Ala Trp Tyr Tyr Ser Val Gly Gln Tyr Ala Ala
1               5                   10                  15

Lys Met Thr Arg Ala Leu Ala Glu Arg Tyr Lys Asp His Pro Ala Leu
            20                  25                  30

Ala Leu Trp His Val Asp Asn Glu Leu Gly Cys His Val Ser
        35                  40                  45

<210> SEQ ID NO 12
<211> LENGTH: 44
<212> TYPE: PRT
<213> ORGANISM: Escherichia coli

<400> SEQUENCE: 12

His Trp Arg Ala Thr Ser Pro Val Phe Leu Asp Tyr Ala Leu Asn Leu
1               5                   10                  15

Cys Arg Lys Met Ala Glu His Tyr Lys Asp Asn Pro Tyr Val Val Ser
            20                  25                  30

Trp His Val Ser Asn Glu Tyr Gly Cys His Asn Arg
        35                  40

<210> SEQ ID NO 13
<211> LENGTH: 44
<212> TYPE: PRT
<213> ORGANISM: Escherichia coli

<400> SEQUENCE: 13

His Trp Arg Pro Thr Ser Pro Val Phe Arg Glu Tyr Ala Leu Arg Leu
1               5                   10                  15

Cys Arg Ala Met Ala Glu His Tyr Arg Asp Asn Pro Tyr Val Val Ala
            20                  25                  30

Trp His Val Ser His Glu Tyr Gly Cys His Asn Arg
        35                  40

<210> SEQ ID NO 14
<211> LENGTH: 44
<212> TYPE: PRT
<213> ORGANISM: Escherichia coli

<400> SEQUENCE: 14

Asn Ser Cys Pro Asn Ser Pro Thr Tyr Arg Lys Tyr Ser Glu Lys Ile
1               5                   10                  15

Ala Asp Lys Leu Ala Glu Arg Tyr Lys Asp His Pro Ala Val Leu Val
            20                  25                  30

Trp His Ile Ser Asn Glu Tyr Gly Gly Asp Cys Tyr
        35                  40

<210> SEQ ID NO 15
<211> LENGTH: 44
<212> TYPE: PRT
<213> ORGANISM: Escherichia coli

<400> SEQUENCE: 15

Asn His Cys Tyr Thr Ser Pro Val Tyr Arg Glu Lys Val Thr Ala Ile
1               5                   10                  15

Asn Thr Lys Leu Ala Glu Arg Tyr Ser Asp His Pro Ala Val Ile Gly
            20                  25                  30

Trp His Ile Ser Asn Glu Phe Gly Gly Asp Cys His

-continued

```
                35                  40

<210> SEQ ID NO 16
<211> LENGTH: 44
<212> TYPE: PRT
<213> ORGANISM: Escherichia coli

<400> SEQUENCE: 16

Asn His Cys Tyr Thr Ser Pro Ile Tyr Arg Glu Lys Ile Ala Ile Ile
 1               5                  10                  15

Asp Arg Leu Leu Ala Glu Arg Tyr Lys Asp His Pro Ala Leu Ile Leu
            20                  25                  30

Trp His Ile Ser Asn Glu Phe Glu Gly Gln Cys Tyr
        35                  40

<210> SEQ ID NO 17
<211> LENGTH: 42
<212> TYPE: PRT
<213> ORGANISM: Escherichia coli

<400> SEQUENCE: 17

Arg Trp Gly Gly Met Glu Thr Gly Gly Asn Pro Glu Arg Pro Pro His
 1               5                  10                  15

Arg Ser Ser Ala Thr Gly Thr Thr Arg Leu Ser Tyr Ile Trp Gly Val
            20                  25                  30

Arg Ile Asn Glu Ser Gln Asp Ser His Asp
        35                  40

<210> SEQ ID NO 18
<211> LENGTH: 44
<212> TYPE: PRT
<213> ORGANISM: Escherichia coli

<400> SEQUENCE: 18

Gln Tyr Ile Gly Asn Ser Glu Trp Lys Lys Val Ala Glu Gln Asn Leu
 1               5                  10                  15

Arg Glu Met Ile Thr Arg Asp Trp Asn His Pro Ser Ile Ile Leu Trp
            20                  25                  30

Gly Val Arg Ile Asn Glu Ser Gln Asp Asp Ala
        35                  40

<210> SEQ ID NO 19
<211> LENGTH: 44
<212> TYPE: PRT
<213> ORGANISM: Escherichia coli

<400> SEQUENCE: 19

Gln His Ile Gly Asp Glu Asn Trp Lys Asn Ile Ala Lys Glu Asn Leu
 1               5                  10                  15

Lys Glu Met Ile Leu Arg Asp Arg Asn His Pro Cys Ile Phe Met Trp
            20                  25                  30

Gly Val Arg Ile Asn Glu Arg Leu Asp Asp His Asp
        35                  40

<210> SEQ ID NO 20
<211> LENGTH: 43
<212> TYPE: PRT
<213> ORGANISM: Escherichia coli

<400> SEQUENCE: 20

Ala Val Leu Gly Gly Asp Lys Asp Glu Thr Trp Ala Lys Phe Asp Leu
```

```
            1               5                  10                 15
Thr Ser Thr Ile Asn Arg Asp Arg Asn Ala Pro Ser Val Ile Met Trp
                    20                  25                 30

Ser Leu Gly Asn Glu Met Met Glu Gly Ile Ser
            35                  40
```

<210> SEQ ID NO 21
<211> LENGTH: 44
<212> TYPE: PRT
<213> ORGANISM: Escherichia coli

<400> SEQUENCE: 21

```
Asn Ile Pro Ala Ser Glu Pro Glu Trp Leu Pro Ala Cys Leu Asp Arg
 1               5                  10                 15

Ala Asn Asn Met Phe Gln Arg Asp Lys Asn His Ala Ser Val Ile Ile
                    20                  25                 30

Trp Ser Cys Gly Asn Glu Ser Tyr Ala Gly Lys Asp
            35                  40
```

<210> SEQ ID NO 22
<211> LENGTH: 44
<212> TYPE: PRT
<213> ORGANISM: Escherichia coli

<400> SEQUENCE: 22

```
Asn Val Pro Gly Ser Leu Pro Gln Trp Gln Ala Ala Val Leu Asp Arg
 1               5                  10                 15

Ala Ser Ser Met Val Glu Arg Asp Lys Asn His Pro Ser Val Leu Ile
                    20                  25                 30

Trp Ser Cys Gly Asn Glu Ser Tyr Ala Gly Glu Asp
            35                  40
```

<210> SEQ ID NO 23
<211> LENGTH: 44
<212> TYPE: PRT
<213> ORGANISM: Escherichia coli

<400> SEQUENCE: 23

```
Asn Val Pro Gly Asp Asn Pro His Trp Pro Ala Ala Val Ile Asp Arg
 1               5                  10                 15

Ala Arg Ser Asn Tyr Glu Trp Phe Lys Asn His Pro Ser Ile Ile Phe
                    20                  25                 30

Trp Ser Leu Gly Asn Glu Ser Tyr Ala Gly Glu Asp
            35                  40
```

<210> SEQ ID NO 24
<211> LENGTH: 44
<212> TYPE: PRT
<213> ORGANISM: Escherichia coli

<400> SEQUENCE: 24

```
Asn Val Pro Gly Ser Tyr Asp Glu Trp Glu Ala Ala Thr Leu Asp Arg
 1               5                  10                 15

Ala Arg Thr Asn Phe Glu Thr Phe Lys Asn His Val Ser Ile Leu Phe
                    20                  25                 30

Trp Ser Leu Gly Asn Glu Ser Tyr Ala Gly Ser Val
            35                  40
```

<210> SEQ ID NO 25
<211> LENGTH: 44

```
<212> TYPE: PRT
<213> ORGANISM: Escherichia coli

<400> SEQUENCE: 25

Asn Val Pro Gly Asp Asp Gln His Trp Leu Gly Ala Ser Leu Ser Arg
  1               5                  10                  15

Val Lys Asn Met Met Ala Arg Asp Lys Asn His Ala Ser Ile Leu Ile
             20                  25                  30

Trp Ser Leu Gly Asn Glu Ser Tyr Ala Gly Thr Val
             35                  40

<210> SEQ ID NO 26
<211> LENGTH: 44
<212> TYPE: PRT
<213> ORGANISM: Escherichia coli

<400> SEQUENCE: 26

Ile Val Pro Gly Ser Lys Arg Glu Trp Glu Gly Ala Cys Val Asp Arg
  1               5                  10                  15

Val Asn Ser Met Met Arg Arg Asp Tyr Asn His Pro Ser Val Leu Ile
             20                  25                  30

Trp Ser Leu Gly Asn Glu Ser Tyr Val Gly Asp Val
             35                  40

<210> SEQ ID NO 27
<211> LENGTH: 44
<212> TYPE: PRT
<213> ORGANISM: Escherichia coli

<400> SEQUENCE: 27

Ser Val Pro Gly Asp Asp Glu Ala Trp Leu Gly Ala Cys Ile Asp Arg
  1               5                  10                  15

Leu Asp Ser Met Ile Leu Arg Asp Arg Asn His Pro Ser Val Leu Val
             20                  25                  30

Trp Ser Leu Gly Asn Glu Ser Tyr Ala Gly Glu Val
             35                  40

<210> SEQ ID NO 28
<211> LENGTH: 44
<212> TYPE: PRT
<213> ORGANISM: Escherichia coli

<400> SEQUENCE: 28

Cys Tyr Phe Ala Arg Asp Pro Leu Phe Lys Lys Ala Ile Leu Asp Arg
  1               5                  10                  15

Gln Gln Ala Asn Val Glu Arg Asp Lys Asn Arg Thr Ser Ile Ile Ile
             20                  25                  30

Trp Ser Leu Gly Asn Glu Ala Gly Tyr Gly Ala Asn
             35                  40

<210> SEQ ID NO 29
<211> LENGTH: 44
<212> TYPE: PRT
<213> ORGANISM: Escherichia coli

<400> SEQUENCE: 29

Asn Ile Ile Ala Asp Asp Ser Lys Phe Glu Thr Ala Ile Ile Glu Arg
  1               5                  10                  15

Ile Glu Ala Ser Ile Met Pro Leu Lys Asn Tyr Ser Ser Ile Val Ser
             20                  25                  30
```

Trp Ser Leu Gly Asn Glu Ser Gly Phe Gly Lys Asn
            35                  40

<210> SEQ ID NO 30
<211> LENGTH: 44
<212> TYPE: PRT
<213> ORGANISM: Escherichia coli

<400> SEQUENCE: 30

Val Thr Leu Ala Asn Arg Trp Glu Trp Lys Ala His Phe Asp Arg
 1               5                  10                  15

Ile Lys Arg Met Val Glu Arg Asp Lys Asn His Pro Ser Ile Ile Phe
                20                  25                  30

Trp Ser Leu Gly Asn Glu Ala Gly Asp Gly Val Asn
            35                  40

<210> SEQ ID NO 31
<211> LENGTH: 44
<212> TYPE: PRT
<213> ORGANISM: Escherichia coli

<400> SEQUENCE: 31

Arg Pro Ile Ala Asp Asn Pro Ala Trp Ile Ala Pro Thr Val Asp Arg
 1               5                  10                  15

Ala Gln Arg Ser Val Glu Arg Asp Lys Asn His Ala Ser Ile Ile Phe
                20                  25                  30

Trp Ser Met Gly Asn Glu Cys Ala Tyr Gly Cys Thr
            35                  40

<210> SEQ ID NO 32
<211> LENGTH: 44
<212> TYPE: PRT
<213> ORGANISM: Escherichia coli

<400> SEQUENCE: 32

Asn Arg Leu Ser Asp Asp Pro Ala Trp Leu Pro Ala Phe Ser Ala Arg
 1               5                  10                  15

Val Thr Arg Met Val Gln Ser Asn Arg Asn His Pro Cys Ile Ile Ile
                20                  25                  30

Trp Ser Leu Gly Asn Glu Ser Gly Gly Gly Gly Asn
            35                  40

<210> SEQ ID NO 33
<211> LENGTH: 44
<212> TYPE: PRT
<213> ORGANISM: Escherichia coli

<400> SEQUENCE: 33

Asn Arg Leu Thr Asn Asp Pro Thr Tyr Leu Pro Leu Met Ser Glu Arg
 1               5                  10                  15

Val Thr Arg Met Val Met Arg Asp Arg Asn His Pro Ser Ile Ile Ile
                20                  25                  30

Trp Ser Leu Gly Asn Glu Ser Gly Tyr Gly Ser Asn
            35                  40

<210> SEQ ID NO 34
<211> LENGTH: 44
<212> TYPE: PRT
<213> ORGANISM: Escherichia coli

<400> SEQUENCE: 34

-continued

Asn Arg Leu Thr Asp Asp Pro Arg Trp Leu Pro Ala Met Ser Glu Arg
 1               5                  10                  15

Val Thr Arg Met Val Gln Arg Asp Arg Asn His Pro Ser Val Ile Ile
                20                  25                  30

Trp Ser Leu Gly Asn Glu Ser Gly His Gly Ala Asn
                35                  40

<210> SEQ ID NO 35
<211> LENGTH: 44
<212> TYPE: PRT
<213> ORGANISM: Escherichia coli

<400> SEQUENCE: 35

Ser Arg Leu Ala Asp Asp Pro Arg Trp Leu Pro Ala Met Ser Glu Arg
 1               5                  10                  15

Val Thr Arg Met Val Gln Arg Asp Arg Asn His Pro Ser Ile Ile Ile
                20                  25                  30

Trp Ser Leu Gly Asn Glu Ser Gly His Gly Ala Asn
                35                  40

<210> SEQ ID NO 36
<211> LENGTH: 46
<212> TYPE: PRT
<213> ORGANISM: Escherichia coli

<400> SEQUENCE: 36

Glu Gly Leu His Glu Asp Gly Asp Phe Leu Thr His Glu Lys Met Asp
 1               5                  10                  15

Asp Phe Val Glu Tyr Ala Asp Tyr Cys Phe Lys Glu Phe Pro Glu Val
                20                  25                  30

Lys Tyr Trp Ile Thr Ile Asn Glu Ile Arg Ser Val Ala Val
                35                  40                  45

<210> SEQ ID NO 37
<211> LENGTH: 46
<212> TYPE: PRT
<213> ORGANISM: Escherichia coli

<400> SEQUENCE: 37

Glu Val Leu His Lys Asp Gly Asp Phe Leu Asn Arg Lys Thr Ile Asp
 1               5                  10                  15

Tyr Phe Val Asp Tyr Ala Glu Tyr Cys Phe Lys Glu Phe Pro Glu Val
                20                  25                  30

Lys Tyr Trp Thr Thr Phe Asn Glu Ile Gly Pro Ile Gly Asp
                35                  40                  45

<210> SEQ ID NO 38
<211> LENGTH: 46
<212> TYPE: PRT
<213> ORGANISM: Escherichia coli

<400> SEQUENCE: 38

Glu Ala Leu His Ser Asn Gly Asp Phe Leu Asn Arg Glu Asn Ile Glu
 1               5                  10                  15

His Phe Val Asn Tyr Ala Glu Phe Cys Phe Lys Glu Phe Ser Glu Val
                20                  25                  30

Asn Tyr Trp Thr Thr Phe Asn Glu Ile Gly Pro Ile Gly Asp
                35                  40                  45

<210> SEQ ID NO 39

```
<211> LENGTH: 46
<212> TYPE: PRT
<213> ORGANISM: Escherichia coli

<400> SEQUENCE: 39

Glu Ala Leu His Ser Asn Gly Asp Phe Leu Asn Arg Glu Asn Ile Glu
 1               5                  10                  15

His Phe Ile Asp Tyr Ala Ala Phe Cys Phe Glu Glu Phe Pro Glu Val
                20                  25                  30

Asn Tyr Trp Thr Thr Phe Asn Glu Ile Gly Pro Ile Gly Asp
            35                  40                  45

<210> SEQ ID NO 40
<211> LENGTH: 47
<212> TYPE: PRT
<213> ORGANISM: Escherichia coli

<400> SEQUENCE: 40

Gly Asp Phe Thr Gly Pro Ser Gly Trp Leu Ser Thr Arg Thr Val Tyr
 1               5                  10                  15

Glu Phe Ala Arg Phe Ser Ala Tyr Ile Ala Trp Lys Phe Asp Asp Leu
                20                  25                  30

Val Asp Glu Tyr Ser Thr Met Asn Glu Pro Asn Val Val Gly Gly
            35                  40                  45

<210> SEQ ID NO 41
<211> LENGTH: 47
<212> TYPE: PRT
<213> ORGANISM: Escherichia coli

<400> SEQUENCE: 41

Gly Asp Phe Thr Gly Pro Thr Gly Trp Leu Asn Ser Arg Thr Val Tyr
 1               5                  10                  15

Glu Phe Ala Arg Phe Ser Ala Tyr Val Ala Trp Lys Leu Asp Asp Leu
                20                  25                  30

Ala Ser Glu Tyr Ala Thr Met Asn Glu Pro Asn Val Val Trp Gly
            35                  40                  45
```

US 6,555,348 B2

ENZYME ISOLATED FROM A BIFIDOBACTERIUM

This application claims the benefit of Provisional application No. 60/207,154, filed May 26, 2001.

TECHNICAL FIELD OF INVENTION

The present invention concerns improvement of fermented dairy products. In particular, the invention concerns a β-galactosidase with transgalactosylating activity. More particularly, the invention concerns a β-galactosidase isolated from *Bifidobacterium bifidum* where the C-terminal end of the protein has been deleted and the resulting truncated enzyme has higher transgalactosylating activity than hydrolase activity. When lactose is used as a substrate, galacto-oligosaccharides are products of the transgalactosylase activity. Galacto-oligosaccharides enhance growth of health-promoting Bifidobacterium that may be used in a number of applications in the dairy industry.

BACKGROUND OF THE INVENTION

The genus Bifidobacterium is one of the most commonly used types of bacteria cultures in the dairy industry for fermenting a variety of dairy products. Ingestion of Bifidobacterium-containing products furthermore has a health-promoting effect. This effect is not only achieved by a lowered pH of the intestinal contents, but also by the ability of Bifidobacterium to repopulate the intestinal flora in individuals who have had their intestinal flora disturbed by, for example, intake of antibiotics. Bifidobacterium furthermore has the potential of outcompeting potential harmful intestinal micro-organisms.

Galacto-oligosaccharides are known to enhance the growth of Bifidobacterium. This effect is likely achieved through the unique ability of Bifidobacterium to exploit galacto-oligosaccharides as a carbon source. Dietary supplement of galacto-oligosaccharides is furthermore thought to have a number of long-term disease protecting effects. For example, galacto-oligosaccharide intake has been shown to be highly protective against development of colorectal cancer in rats (Wijnands, et al., 1999). There is therefore a great interest in developing cheap and efficient methods for producing galacto-oligosaccharides for use in the industry for improving dietary supplements and dairy products.

The enzyme β-galactosidase (EC 3.2.1.23) usually hydrolyzes lactose to the monosaccharides D-glucose and D-galactose. In the normal enzyme reaction of β-galactosidases, the enzyme hydrolyzes lactose and transiently binds the galactose monosaccharide in a galactose-enzyme complex that transfers galactose to the hydroxyl group of water, resulting in the liberation of D-galactose and D-glucose. However, at high lactos concentrations, some β-galactosidases are able to transfer galactose to the hydroxyl groups of D-galactose or D-glucose in a process called transgalactosylation, whereby galacto-oligosaccharides are produced.

Enzymes capable of transgalactosylation have been isolated from a wide range of micro-organisms, including bacteria and yeasts. The observation that galacto-oligosaccharides enhance the growth of health-promoting Bifidobacterium has stimulated investigations of Bifidobacterium and their β-galactosidase enzymes. Two DNA sequences of *B. breve* and *B. longum* β-galactosidase genes have been deposited in GeneBank (accession numbers E5040 and AJ242596, respectively). Dumortier et al. (1994) have reported that *B. bifidum* DSM 20215 contains three β-galactosidases and one of these enzymes has transgalactosylating properties. However, no identification of the enzyme possessing this activity or any sequence of the enzyme or the corresponding gene from *B. bifidum* DSM 20215 has been published.

Production of galacto-oligosaccharides by the use of β-galactosidases has been reported in several papers. For example, β-galactosidase from *E. coli* has been shown to produce oligosaccharides at high lactose concentrations (0.5 M or approximately 20% lactose; Huber et al. 1976). Various thermophilic microorganisms have been shown to produce oligosaccharides at high temperatures and high lactose concentrations, e.g. *Sterigmatomyces elviae* can produce 39% oligosaccharides from 20% lactose at 60° C. (onishi & Tanaka, 1995), and *Saccharopolyspora rectivirgula* can synthesize 41% oligosaccharides in 1.75 M lactose at 70° C. (Nako et al., 1994).

However, the enzymes described above all have the drawbacks of requiring either high temperatures or high lactose concentrations or both in order to exhibit significant transgalactosylase activity. There is thus a need for developing cheaper and more efficient methods of producing galacto-oligosaccharides for use in the industry.

SUMMARY OF THE INVENTION

The present invention describes a new β-galactosidase from *Bifidobacterium bifidum*. A truncated version of the enzyme has surprisingly been shown to have a high transgalactosylating activity. When the truncated enzyme, or a host cell expressing the recombinant truncated enzyme, is incubate with lactose under appropriate conditions, galacto-oligosaccharides are produced at a high efficiency. Presence of galacto-oligosaccharides in dairy products or other comestible products has the advantage of enhancing the growth of health-promoting Bifidobacterium in the product or in the intestinal flora of the consumer after intake of the product, or both.

BRIEF DESCRIPTION OF THE DRAWINGS

FIGS. 1(A–C):

Figure 3:
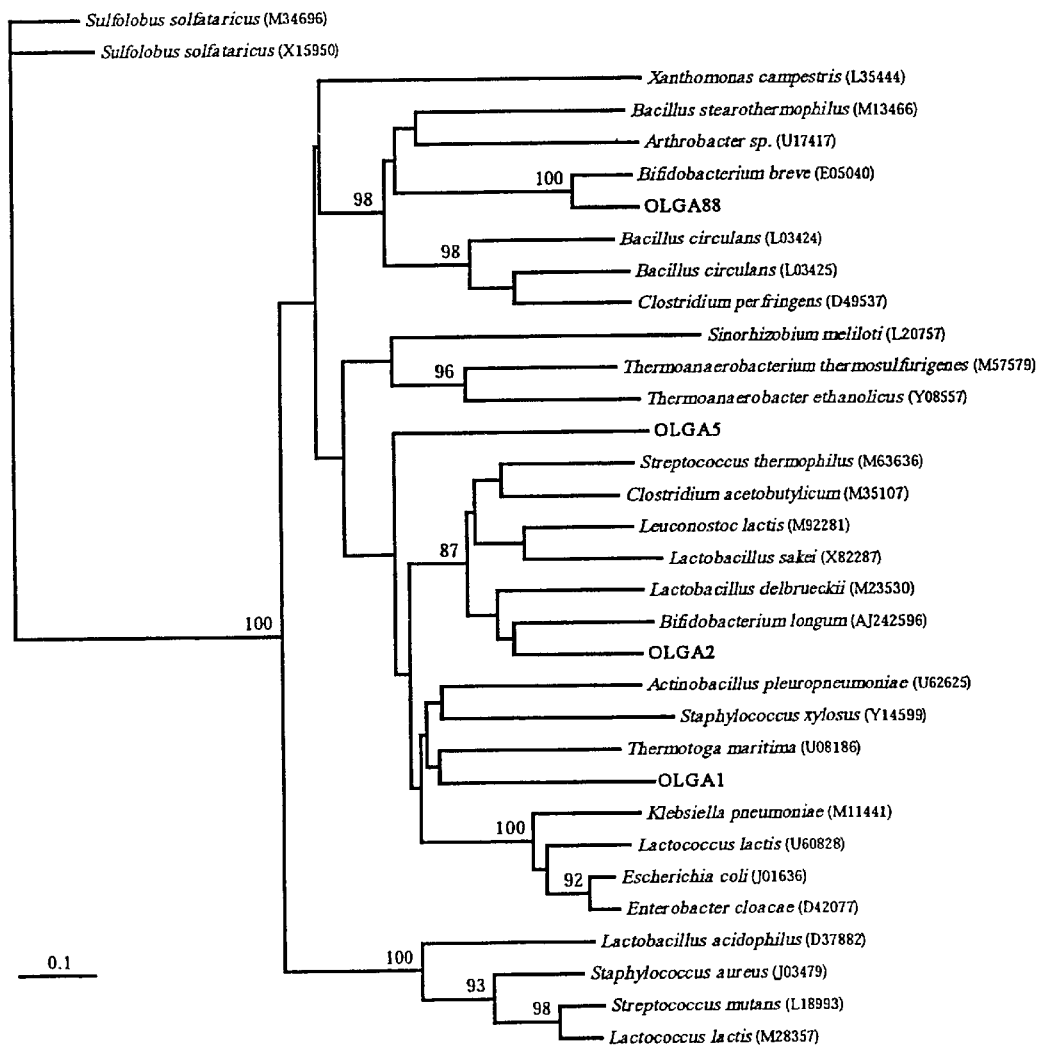

OLGA5 sequence. DNA (SEQ ID NO:1) and protein (SEQ ID NO:2) sequence of the OLGA5 β-galactosidase from *Bifidobacterium bifidum*. The signal sequence is shown in bold and the part of the OLGA5 gene deleted in OLGA347 is shown in italics. The BglII site used to create the deletion is highlighted.

FIG. 2:

Comparison of β-galactosidase active site regions. Alignment of regions around the catalytic Glu461 residue (highlighted) from *E. coli* (SEQ ID NOs:9–41). The sequences are identified by their database accession numbers. 6-phospho-β-galactosidase sequences are marked with a (P).

FIG. 3:

Neighbour joining analysis of the alignment in FIG. 1, where the Sulfolubus sequences were used as an outgroup. Results from a bootstrap analysis (n=100) are shown for the junctions with a value above 80.

FIG. 4:

OLGA5 transgalactosylase activity. Total cell lysate of *E. coli* cells harbouring the OLGA5 gene in a plasmid were incubated with 0.4 M lactose at 37° C. for 20 hours. A 50 μl total reaction volume contained the indicated amounts of total cell lysate. Reaction samples were analysed on a silica gel TLC plate. The plate was sprayed with Orcinol reagent to visualise the sugars.

FIG. 5:

C-terminal deletions of OLGA5 β-galactosidase. A 1752 amino acid open reading frame encodes the OLGA5 β-galactosidase, where the starting 32 amino acids likely represent a signal peptide (white box). Deletion mutants of OLGA5 were constructed using the indicated restriction sites. OLGA342=bp 212–5021 (PstI site), aa 1–1604, (SEQ ID NO:3, SEQ ID NO:4); OLGA345=bp 212–4190 (EcoRI site), aa 1–1327, (SEQ ID NO:5, SEQ ID NO:6); OLGA347=bp 212–3729 (BglII site), aa 1–1174, (SEQ ID NO:7, SEQ ID NO:8); OLGA344=bp 212–3159 (Bg/II site), aa 1–983 (SEQ ID NO:9, SEQ ID NO:10). Deletion mutants of OLGA5 were constructed using the indicated restriction sites. Lysates prepared from bacterial cultures grown over night were used for measurement of β-galactosidase activity, and the relative results are shown to the right of the respective constructs. Restriction enzyme symbols used: BglII (B), EcoRI (E), EcoRV (V), HindIII (H), KpnI (K), NruI (N), PstI (P).

FIG. 6:

TLC analysis of transgalactosylase activity. Total cell lysates for the two tested deletion mutants, OLGA347 and OLGA345, were used in the indicated amounts to react with 0.4 M lactose in 50 µl total volume. The reactions were incubated at 37° C. for 20 hours. Samples were analysed on a silica gel TLC plate. The plate was sprayed with Orcinol reagent to visualise the sugars.

FIGS. 7(A–B):

Oligosaccharides produced by OLGA347. The indicated amounts of OLGA347 total cell lysate were incubated with 15% lactose in a total volume of µl for 21 hours at 37° C. Radioactive lactose that was labelled with $^{14}C$ in the glucose C-1 position was used. Samples were separated on a TLC plate and quantitated by use of a phospho-imager. A: Image used for measurement of $^{14}C$-signals from lactose, glucose and galacto-oligosaccharides (GOS) spots. B: Measured $^{14}C$-signals after subtraction of background (blind lane).

FIGS. 8(A–D):

HPLC measurement of OLGA347 enzyme reaction products. Reactions in 10%, 20% and 40% lactose were performed using the indicated amounts of OLGA347 total cell lysate. A total volume of 200 µl was used and the reactions were incubated at 37° C. for 20 hours. Diluted samples were subjected to HPLC analysis and standard curves were used to convert the observed peak areas to concentrations (mg/ml). A: Obtained mg/ml saccharide after OLGA347 reaction with 10% lactose. B: Obtained mg/ml saccharide after OLGA347 reaction with 20% lactose. C: Obtained mg/ml saccharide after OLGA347 reaction with 40% lactose. D: Plot of results from the 10% reaction. The resulting amount of galacto-oligosaccharides is calculated as the amount of lactose not recovered as glucose or galactose ("GOS").

DETAILED DESCRIPTION OF THE INVENTION

The first aspect of the invention concerns a new β-galactosidase, OLGA5 (SEQ ID NO:1 and SEQ ID NO:2), from *Bifidobacterium bifidum* that has been isolated and characterised. *E. coli* cells were transformed with a plasmid containing insertions consisting of PstI digested chromosomal DNA from *B. bifidum*. Clones with β-galactosidase activity were selected on plates containing a chromogenic β-galactosidase substrate. One of the positive colonies contained a plasmid with an insert of approximately 20 kb, pOLGA5 (SEQ ID NO:1). Sequencing of the DNA sequence revealed that the deduced amino acid sequence of OLGA5 β-galactosidase (SEQ ID NO:2) is approximately twice as long as the presently known β-galactosidases and it furthermore shows a surprisingly low degree of sequence homology with known β-galactosidases. Expression of recombinant OLGA5 in *E. coli* revealed that the enzyme, in addition to lactose hydrolysing activity, also exhibited transgalactosylating activity. The C-terminal part of the OLGA5 enzyme showed no homology to known β-galactosidases. A variety of OLGA5 C-terminal deletion mutants were subsequently constructed and the resulting enzymes were investigated for their hydrolytic and transgalactosylating activity.

A second aspect of the invention concerns deletion mutants of OLGA5, e.g. OLGA347. Out of several C-terminal deletion mutants, OLGA347 which has a 578 amino acid C-terminal deletion, showed the most pronounced increased level of oligosaccharides produced when incubated with lactose even at relatively low lactose concentrations. The enzyme apparently transferred virtually all galactose molecules onto galactose or glucose. Deletion of the C-terminal end of OLGA5 hence converted the enzyme from a hydrolytic OLGA5 β-galactosidase to a transgalactosylating OLGA347-transgalactosidase. Unlike other transgalactosylating β-galactosidases, including the native OLGA5 enzyme, the truncated β-galactosidase OLGA347 transfers galactose onto acceptor sugar molecules at high frequency at all lactose concentrations examined.

In one embodiment, an expression vector with an insert encoding OLGA5, OLGA342, OLGA345, OLGA347, OLGA344, or any other OLGA5 variant is used. This expression vector can be transformed into a host cell selected from the group comprising Bifidobacterium, Lactococcus, Lactobacillus, Streptococcus, Leuconostoc, Escherichia, Bacillus, Streptomyces, Saccharomyces, Kluyveromyces, Candida, Torula, Torulopsis and Aspergillus. A cell of the genus Bifidobacterium is selected from the group consisting of *Bifidobacterium breve, Bifidobacterium longum, Bifidobacterium infantis, Bifidobacterium bifidum* and *Lactococcus lactis*. The cell is then cultured in a suitable culture medium under conditions permitting expression of for example an OLGA5 or an OLGA347 variant and the resulting enzyme is thereafter recovered from the culture.

In another embodiment of the invention, an OLGA5 variant is part of an expression vector, which can be transformed into any one of the above, mentioned host cells. The cell is then cultured in a suitable culture medium under conditions permitting expression of the OLGA5 variant and the resulting enzyme is thereafter recovered from the culture. The OLGA5 variant may contain any random mutation or any mutation generated by conventional molecular biology techniques. Any fragment of a mutated or a wild-type OLGA5 DNA molecule can be inserted into the expression vector. The fragment can be generated by PCR (polymerase chain reaction) or by means of any restriction sites present in the sequence or a combination of both. The procedures for generating OLGA5 variants are well known to a person skilled in the art. It is thus not critical to the present invention in which way the variant is obtained. The variants disclosed in the present text are obtained by subcloning by use of restriction sites present in the sequence.

Another aspect of the invention concerns use of one or more of the above mentioned cell types for producing a product selected from the group consisting of yoghurt, cheese, fermented dairy products, dietary supplements and probiotic comestible products. In this aspect, the technical effect of the enhanced growth of Bifidobacterium is used for improving the quality of the industrial products. Addition of galacto-oligosaccharides enhances the growth of health-promoting Bifidobacterium. Galacto-oligosaccharides produced by OLGA347 is thus much cheaper and easier to obtain compared to using native β-galactosidases for producing oligosaccharides.

Yet another aspect of the invention concerns the use of OLGA5, OLGA342, OLGA345, OLGA347, OLGA344 or any other OLGA5 variant or the use of any one or more of the above mentioned cell types for producing oligosaccharides. The oligosaccharides comprise, but are not limited to fructooligo-saccharides, galacto-oligosaccharides, isomalto-oligosaccharides, malto-oligosaccharides, lacto-sucrose and xylo-oligosaccharides.

In one embodiment of the invention, the oligosaccharides are produced by incubating the cell expressing the OLGA5 variant in a medium that comprises a disaccharide substrate such as for example lactulose, trehalose, rhamnose, maltose, sucrose, lactose, or cellobiose. The incubation is carried out under conditions where oligosaccarides are produced. The cells may be part of a product selected from the group consisting of yoghurt, cheese, fermented milk products, dietary supplements, and probiotic comestible products. Alternatively, the oligo-saccharides can be recovered and subsequently be added to the product of interest before or after its preparation. Addition of oligosaccharides enhance growth of either Bifidobacterium alone or of Bifidobacterium in a mixed culture.

In another embodiment, the oligosaccharides are produced by incubating the OLGA5 variant in a medium that comprises a disaccharide substrate such as, for example, lactulose, trehalose, rhamnose, maltose, sucrose, lactose, or cellobiose. The incubation is carried out under conditions where oligosaccharides are produced. The medium comprising an OLGA5 variant and lactose may be part of a product selected from the group consisting of yoghurt, cheese, fermented milk products, dietary supplements, and probiotic comestible products. Alternatively, the oligo-saccharides can be recovered and subsequently be added to the product of interest before or after its preparation. Addition of oligosaccharides enhances growth of either Bifidobacterium alone or of Bifidobacterium in a mixed culture.

Definitions

"β-galactosidase or a fragment thereof". β-galactosidase is defined as an enzyme capable of hydrolysing lactose to the monosaccharides D-glucose and D-galactose. A fragment of the β-galactosidase comprises 5–98%, preferably 40–95% and most preferably 55–75% of the protein and the deletion preferably concerns the C-terminal end.

A "host cell" is selected from the group consisting of: fungi, yeasts, and prokaryotes. The micro-organism is more preferably a prokaryote and most preferably a bacterium of the genus Bifidobacterium or the species E. coli.

By "oligosaccharides" is meant an oligosaccharide consisting of at least three sugar molecules. An example of an oligosaccharide, which is not meant to be limiting, is galacto-oligosaccharide. The linkages between the sugar residues of the oligosaccharide comprise but are not limited to 1–4 and 1–6 bindings.

Incubation of β-galactosidase with lactose takes place in the presence of 0.5–60% lactose, preferably 2–30% lactose and most preferably 2–15% lactose.

Conditions of incubating β-galactosidase with lactose are defined by performing the incubation at a temperature between 5 and 75° C., preferably 15–45° C., and most preferably at 37° C. The time required for the incubation is 1–50 hours, preferably 5–40 hours and most preferably 15–25 hours.

A "comestible product" comprises a product intended for ingestion such as foods, drinks, tablets, and powders.

EXAMPLES

Example 1

Isolation and characterisation of transgalactosylating β-galactosidase from B. bifidum. PstI digested chromosomal DNA from B. bifidum DSM 20215 was ligated into pKS plasmid (Stratagene) using standard procedures. The ligation mixture was transformed into E. coli strain MT102 defective in LacZ and β-galactosidase. β-galactosidase producing clones were identified as blue colonies on plates containing the chromogenic β-galactosidase substrate X-gal.

One of the blue colonies contained a plasmid with an insert of approximately 20 kb, pOLGA5. The insert was further subcloned and partly sequenced and an open reading frame encoding a putative β-galactosidase (OLGA5 β-galactosidase) was identified (FIG. 1). BLAST search showed that OLGA5 β-galactosidase showed the highest degree of homology with Streptomyces coelicolor β-galactosidase (AL133171) and Thermoanaerobacter ethanolicus (YO8557) with 38% and 30% identity, respectively. FIG. 3 shows an "identity tree" of OLGA5 and related amino acid sequences.

A detailed analysis of the amino acid sequence of OLGA5 β-galactosidase revealed that the enzyme contains a putative signal sequence at its N-terminal and that the open reading frame encodes a polypeptide of 185 kDa which is approximately twice as large as any of the presently known β-galactosidases. Recombinant OLGA5 enzyme produced in E. coli was purified and N-terminal amino acid sequencing confirmed, that the signal sequence was cleaved during expression in E. coli. SDS-PAGE confirmed the molecular weight of the OLGA5 polypeptide.

Figure 4:
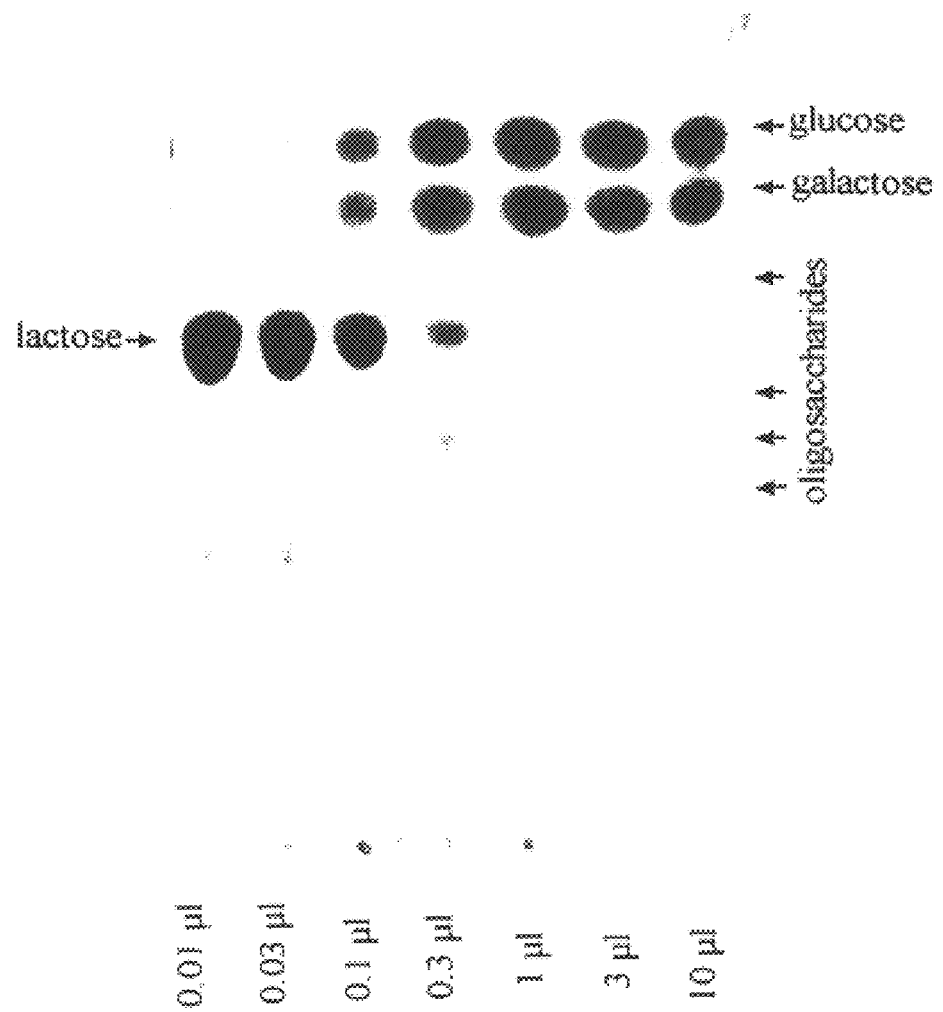

Cellular extracts of recombinant E. coli MT102 containing pOLGA5 were prepared and analysed for transgalactosylating activity. FIG. 4 shows that OLGA5, in addition to lactose hydrolysing activity, also exhibited transgalactosylating activity.

Example 2

Figure 5:
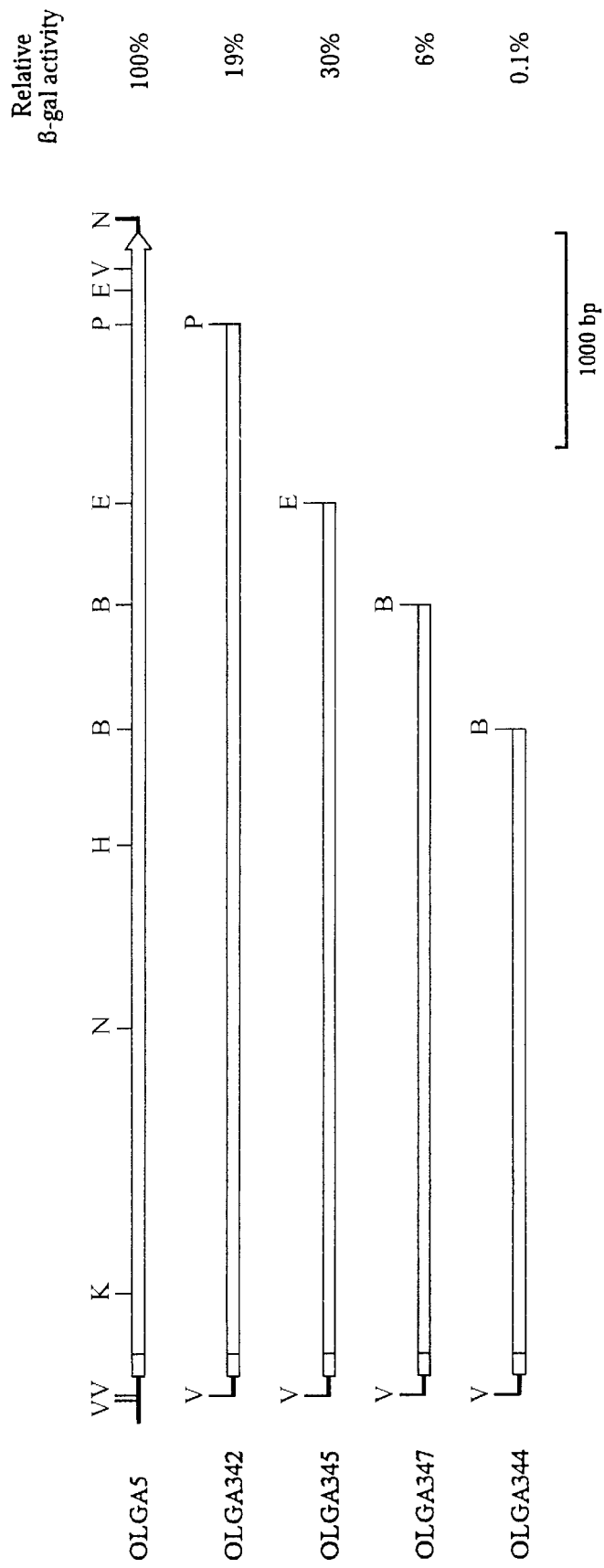
Figure 6:
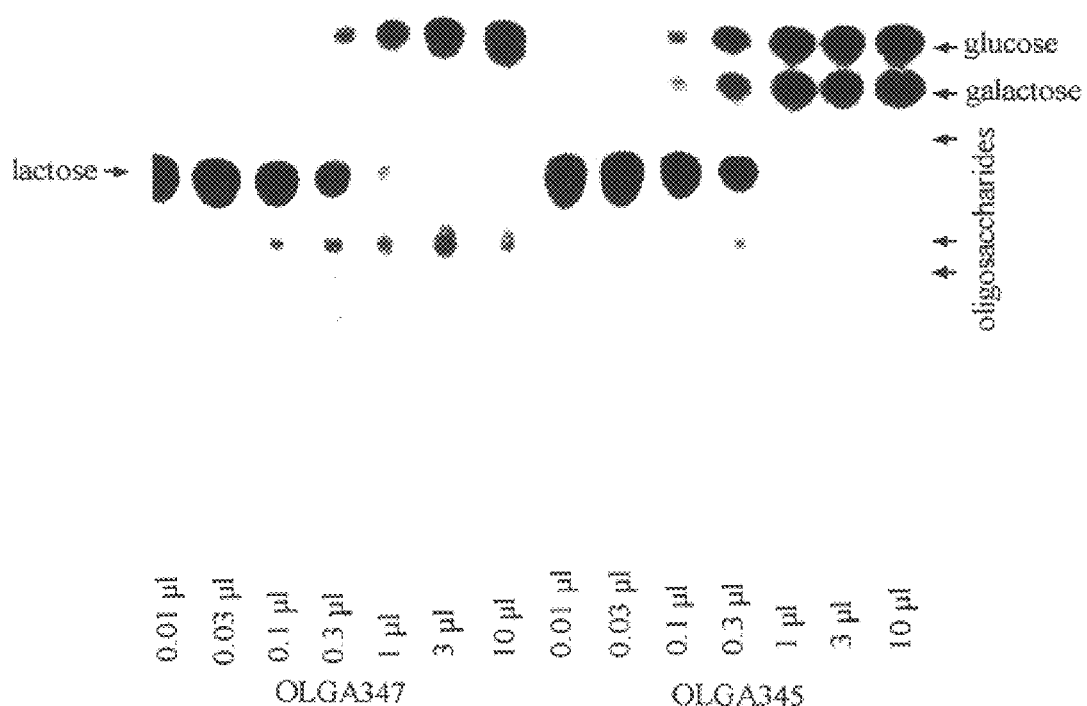

Construction of a truncated OLGA5 β-galactosidase with high transgalactosylase activity The region of OLGA5 homologous to other β-galactosidases is located in the N-terminal end of the protein. The C-terminal half showed no homology to any known β-galactosidase However, a sialidase-like galactose-binding domain was observed in the C-terminal part. The role of this C-terminal part of the OLGA5 β-galactosidase was investigated by construction of truncated deletion mutants. The hydrolytic and transgalactosylating activities of the resulting recombinant β-galactosidases were analyzed. FIG. 5 shows that it was possible to delete almost one third of the OLGA5 enzyme and still retain hydrolytic activity.

When the transgalactosylating activity was analysed, similar results were obtained with extracts from E. coli containing the plasmids pOLGA5, pOLGA342, and pOLGA345. However, extracts of cells harbouring pOLGA347 showed an increased level of oligosaccharides produced and almost no galactose. As shown in FIG. 5, an extract containing the truncated OLGA347 β-galactosidase did hydrolyse lactose, but instead of transferring galactose onto hydroxyl groups in water, the enzyme transferred virtually all galactose molecules onto galactose or glucose (or glycerol; the spot migrating slightly slower than glucose on TLC was shown by NMR to be galacto-glycerol—data not shown). In conclusion OLGA347 is a true "transgalactosylase".

Example 3

Characterization of the transgalactosylating activity of OLGA347. Two methods were used to quantitate the transgalactosylating activity of OLGA347 β-galactosidase: TLC analysis of reaction mixtures containing radioactively labelled lactose and HPLC analysis after enzymatic conversion of unlabeled lactose.

Figure 7A:
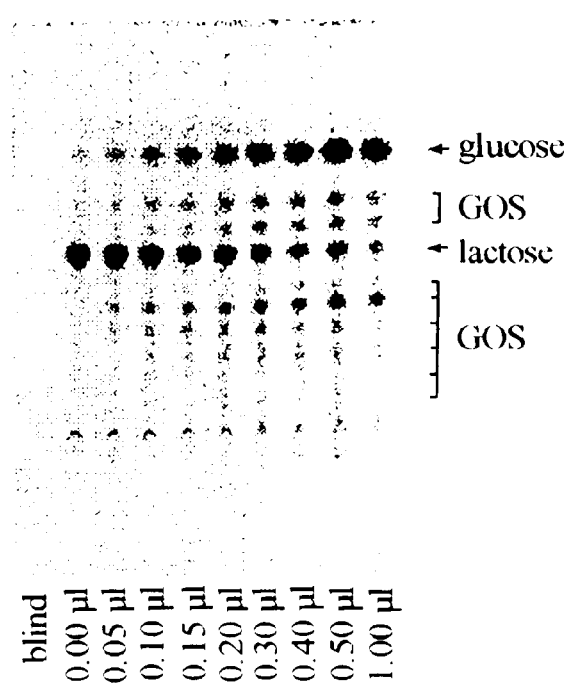
Figure 7B:
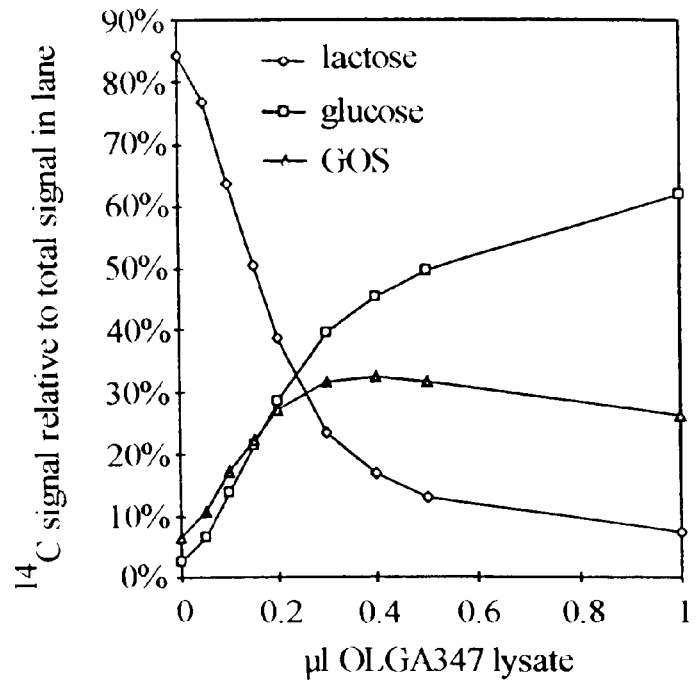

Experiments with radioactivity were carried out with lactose containing the $^{14}$C-label at the C-1 position of glucose. Since the label was in the glucose part of the disaccharide, only reaction products containing glucose were detected. FIG. 7 shows the result of a transgalactosylation experiment with 15% lactose and varying amounts of OLGA347 enzyme. After separation of the reaction mixture by TLC, the plate was scanned and the radioactive spots were quantitated in a phosphoimager. At low enzyme concentrations (between 0 and 0.2 μl of the extract), the glucose and oligosaccharide levels were almost identical, indicating that all glucose molecules were exploited as substrate in transgalactosylation reaction. "Free" hydrolyzed glucose appeared only at high enzyme concentrations.

Figures 8A, 8B, 8C, 8D:
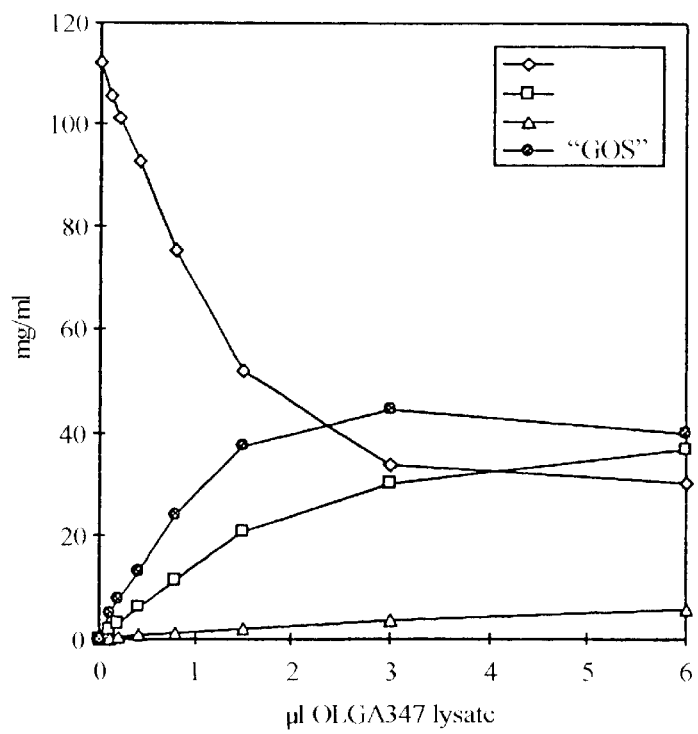

In experiments with unlabelled lactose, different substrate and enzyme concentrations were examined. FIG. 8 shows an experiment in which 10%, 20%, and 40% lactose were used as substrate in enzyme reactions with varying concentrations of OLGA347 enzyme. The reaction mixtures were analyzed with HPLC and the concentrations of lactose, glucose, galactose, and galacto-oligosaccharides were calculated. FIG. 8 shows that, as the enzyme concentration goes up, the lactose concentration is decreased and galactose is produced, indicating that almost all galactose molecules in lactose are transferred onto another sugar. Calculations of carbohydrate concentrations measured in reactions with low enzyme concentrations, indicated that the ratio between glucose and galactose is approximately 0.1, implying that for every lactose molecule hydrolyzed to free galactose and glucose, nine lactose molecules are used in transgalactosylation. As seen in FIG. 8, the transgalactosylating reaction is independent of lactose concentration in the range from 10% to 40% lactose. The maximal yield of galacto-oligosaccharides produced in transgalactosylation reactions with 10%, 20%, or 40% lactose as substrate were 39%, 44%, and 37%, respectively (mg of oligosaccharides produced per mg lactose added).

REFERENCES

Dumortier, V., Brassart, C., and Bouquelet, S. (1994) Purification and properties of a β-D-galactosidase from Bifidobacterium bifidum exhibiting a transgalactosylatjon reaction. Biotechnol. Appl. Biochem. 19, 341-354.

Huber, R. E., Kurz, G., and Wallenfels, K. (1976) A quantitation of the factors which affect the hydrolase and transgalactosylase acticities of β-galactosidase (*E. coli*) on lactose. Biochemistry, 15, 1994

Nakao, M., Harada, M., Kodama, Y., Nakayama, T., Shibano, Y., and Amachi, T. (1994) Purification and haracterization of a thermostable β-galactosidase with high transgalactosylation activity from *Saccharopolyspora rectivirgula*. Appl. Microbiol. Biotechnol. 40, 657–663.

Onishi, N and Tanaka, T. (1995) Purification and properties of a novel thermostable galactooligosaccharide-producing β-galactosidase from Sterigmatomyces elviae CBS8119. Appl. Environ. Microbiol. 61, 4026–4030.

Wijnands, M. V., Appel M. J., Hollanders, V. M., and Woutersen, R. A. (1999) A comparison of the effects of diatary cellulose and fermentable galacto-oligosaccharide in a rat model of colorrectal carcinogenesis: fermentable fibre confers greater protection than non-fermentable fibre in both high and low fat backgrounds. Carcinogenesis. 20, 651–656.

What is claimed is:

1. An isolated or purified enzyme comprising residues 1–1174 of SEQ ID NO:2, or a fragment thereof having transgalactosylating activity, wherein, the ratio of transgalactosylating activity to β-galactosidase activity in a solution of 100 g/L lactose at 37° C. that is higher than 1:1.

2. The enzyme of claim 1, wherein said enzyme comprises residues 1–1174 of SEQ ID NO:2.

3. The fragment of claim 1, said fragment comprising residues 33–1174 of SEQ ID NO:2.

4. An isolated or purified enzyme comprising residues 1–1604 of SEQ ID NO:2, or a fragment thereof having transgalactosylating activity, wherein the ratio of transgalactosylating activity to β-galactosidase activity in a solution of 100 g/L lactose at 37° C. that is higher than 1:1.

5. The fragment of claim 4, wherein said enzyme comprises residues 1–1604 of SEQ ID NO:2.

6. An isolated or purified enzyme comprising residues 1–1327 of SEQ ID NO:2, or a fragment thereof having transgalactosylating activity, wherein the ratio of transgalactosylating activity to β-galactosidase activity in a solution of 100 g/L lactose at 37° C. that is higher than 1:1.

7. The enzyme of claim 6, wherein said enzyme comprises residues 1–327 of SEQ ID NO:2.

8. An isolated or purified enzyme comprising residues 1–983 of SEQ ID NO:2, or a fragment thereof having transgalactosylating activity, wherein the ratio of transgalactosylating activity to β-galactosidase activity in a solution of 100 g/L lactose at 37° C. that is higher than 1:1.

9. The enzyme of claim 8, wherein said enzyme comprises residues 1–983 of SEQ ID NO:2.

10. An isolated or purified fragment of SEQ ID NO:2 having a transgalactosylating activity, wherein said fragment has the amino acid sequence of SEQ ID NO:2 truncated at C-terminal and wherein the ratio of transgalactosylating activity to β-galactosidase activity in a solution of 100 g/L lactose at 37° C. is higher than 1:1.

11. A for producing galacto-oligosaccharides, said process comprising contacting the enzyme or fragment of claims 1, 3, 4, 6, 8 or 10 with a solution of lactose.

12. The process of claim 11, wherein the process is included in a process for producing a yoghurt, a cheese, a fermented dairy product, a dietary supplement, or a probiotic comestible product.

* * * * *

UNITED STATES PATENT AND TRADEMARK OFFICE
CERTIFICATE OF CORRECTION

PATENT NO. : 6,555,348 B2  Page 1 of 1
DATED : April 29, 2003
INVENTOR(S) : Flemming Jørgensen et al.

It is certified that error appears in the above-identified patent and that said Letters Patent is hereby corrected as shown below:

Column 63,
Line 48, "wherein, the" should read -- wherein said enzyme or fragment has the --.
Lines 56 and 63, "wherein the" should read -- wherein said enzyme or fragment has the --.
Line 59, "fragment" should read -- enzyme --.
Line 67, "residues 1-327" should read -- residues 1-1327 --.

Column 64,
Line 47, "wherein the" should read -- wherein said enzyme or fragment has the --.
Line 58, "A for" should read -- A process for --.

Signed and Sealed this

Twenty-sixth Day of August, 2003

JAMES E. ROGAN
*Director of the United States Patent and Trademark Office*